United States Patent
Nickell et al.

(10) Patent No.: US 10,933,131 B2
(45) Date of Patent: Mar. 2, 2021

(54) INCREASED FERTILITY IN BOVINE SPECIES

(71) Applicant: BAYER ANIMAL HEALTH GMBH, Leverkusen (DE)

(72) Inventors: Jason Nickell, Parkville, MO (US); Daniel Keil, Spring Hill, KS (US); Albert Abraham, Shawnee, KS (US); Warren Tully, Auckland (NZ); Richard Gerhardus Martinu Olde Riekerink, Thames (NZ); Terry Settje, Olathe, KS (US); Leland Vickers, Franklin, TN (US); Stuart Nibbelink, Kansas City, MO (US)

(73) Assignee: BAYER ANIMAL HEALTH GMBH, Leverkusen (DE)

( * ) Notice: Subject to any disclaimer, the term of this patent is extended or adjusted under 35 U.S.C. 154(b) by 0 days.

(21) Appl. No.: 16/320,256

(22) PCT Filed: Jul. 25, 2017

(86) PCT No.: PCT/US2017/043662
§ 371 (c)(1),
(2) Date: Jan. 24, 2019

(87) PCT Pub. No.: WO2018/022583
PCT Pub. Date: Feb. 1, 2018

(65) Prior Publication Data
US 2019/0388538 A1 Dec. 26, 2019

Related U.S. Application Data

(60) Provisional application No. 62/366,772, filed on Jul. 26, 2016.

(51) Int. Cl.
| | | |
|---|---|---|
| A61K 39/39 | (2006.01) | |
| A61K 9/127 | (2006.01) | |
| A61P 15/08 | (2006.01) | |
| A61K 39/00 | (2006.01) | |

(52) U.S. Cl.
CPC ........... *A61K 39/39* (2013.01); *A61K 9/1272* (2013.01); *A61P 15/08* (2018.01); *A61K 2039/55555* (2013.01); *A61K 2039/55561* (2013.01)

(58) Field of Classification Search
None
See application file for complete search history.

(56) References Cited

U.S. PATENT DOCUMENTS

| | | | |
|---|---|---|---|
| 4,812,314 A | * | 3/1989 | Barenholz .............. A61K 9/127 424/450 |
| 10,155,950 B2 | * | 12/2018 | Munnes ............... A61K 9/1272 |
| 2012/0064151 A1 | | 3/2012 | Abraham |
| 2013/0295167 A1 | | 11/2013 | Abraham et al. |
| 2014/0010865 A1 | | 1/2014 | Abraham et al. |
| 2018/0312842 A1 | | 11/2018 | Munnes et al. |
| 2018/0326049 A1 | | 11/2018 | Abraham et al. |
| 2019/0008952 A1 | | 1/2019 | Weiss et al. |
| 2019/0201434 A1 | | 7/2019 | Abraham et al. |
| 2019/0233825 A1 | | 8/2019 | Ilg et al. |

FOREIGN PATENT DOCUMENTS

| | | | |
|---|---|---|---|
| RU | 2530520 C1 | * | 10/2013 |
| WO | 2004/050872 A1 | | 6/2004 |
| WO | 2006/017857 A2 | | 2/2006 |
| WO | 2010/130374 A1 | | 11/2010 |
| WO | 2012/084951 A1 | | 6/2012 |
| WO | 2015/128461 A1 | | 9/2015 |

OTHER PUBLICATIONS

PCT International Search Report for PCT/US2017/043662, dated Oct. 11, 2017.
Fair, et al., "The contribution of the maternal immune system to the establishment of pregnancy in cattle," Frontiers in Immunol., (2015), vol. 6, Article 7: 1-7.
Wilson, et al., "Clinical Phase 1 Testing of the Safety and Immunogenicity of an Epitope-Based DNA Vaccine in Human Human Innunodeficiency Virus Type 1-Infected Subjects Receiving Highly Active Antiretroviral Therapy," Clinical and Vaccine Immunol., (2008), vol. 15, No. 6: 986-94.
Singh, et al., "Effectiveness of lipopolysaccharide as an intrauterine immunomodulator in curing bacterial endometritis in repeat breeding cross-bred cows," Animal Reproduction Sci., (2000), vol. 59: 159-166.

* cited by examiner

*Primary Examiner* — Padmavathi Baskar
(74) *Attorney, Agent, or Firm* — McBee Moore & Vanik IP, LLC

(57) ABSTRACT

The present invention relates to compositions and methods for immunomodulation which are effective for increasing conception rate in cows.

10 Claims, 4 Drawing Sheets
Specification includes a Sequence Listing.

SEQUENCE LISTING

```
<160> NUMBER OF SEQ ID NOS: 4

<210> SEQ ID NO 1
<211> LENGTH: 4242
<212> TYPE: DNA
<213> ORGANISM: Artificial sequence
<220> FEATURE:
<223> OTHER INFORMATION: Nucleotide sequence of plasmid pMB75.6

<400> SEQUENCE: 1
ctaaattgta agcgttaata ttttgttaaa attcgcgtta aattttgtt aaatcagctc      60 atttttaac caataggccg aaatcggcaa atcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
```

-continued

```
ctaatcaagt tttttggggt cgaggtgccg taaagcacta aatcggaacc ctaaagggag      300
cccccgattt agagcttgac ggggaaagcc ggcgaacgtg gcgagaaagg aagggaagaa      360
agcgaaagga gcgggcgcta gggcgctggc aagtgtagcg gtcacgctgc gcgtaaccac      420
cacacccgcc gcgcttaatg cgccgctaca gggcgcgtcc cattcgccat tcaggctgcg      480
caactgttgg gaagggcgat cggtgcgggc ctcttcgcta ttacgccagc tggcgaaagg      540
gggatgtgct gcaaggcgat taagttgggt aacgccaggg ttttcccagt cacgacgttg      600
taaaacgacg gccagtgagc gcgcgtaata cgactcacta tagggcgaat tgggtaccgg      660
gccccccctc gagcaggatc tatacattga atcaatattg gcaattagcc atattagtca      720
ttggttatat agcataaatc aatattggct attggccatt gcatacgttg tatctatatc      780
ataatatgta catttatatt ggctcatgtc aatatgacc gccatgttga cattgattat       840
tgactagtta ttaatagtaa tcaattacgg ggtcattagt tcatagccca tatatggagt     900
tccgcgttac ataacttacg gtaaatggcc cgcctggctg accgcccaac gacccccgcc      960
cattgacgtc aataatgacg tatgttccca tagtaacgcc aatagggact ttccattgac     1020
gtcaatgggt ggagtattta cggtaaactg cccacttggc agtacatcaa gtgtatcata     1080
tgccaagtcc gccccctatt gacgtcaatg acggtaaatg gcccgcctgg cattatgccc     1140
agtacatgac cttacgggac tttcctactt ggcagtacat ctacgtatta gtcatcgcta     1200
ttaccatggt gatgcggttt tggcagtaca tcaatgggcg tggatagcgg tttgactcac     1260
ggggatttcc aagtctccac cccattgacg tcaatgggag tttgttttgg caccaaaatc     1320
aacgggactt tccaaaatgt cgtaacaact ccgccccatt gacgcaaatg ggcggtaggc     1380
gtgtacggtg ggaggtctat ataagcagag ctcgtttagt gaaccgtcag atcgcctgga     1440
gacgccatcc acgctgtttt gacctccata agagacaccg gaccgatcc agcctcccct      1500 cgaagccgat ctgataacgg taccgataag ctggcggccg attaagctac agaagttggt      1560
cgtgaggcac tgggcaggta agtatcaagg ttacaagaca ggtttaagga gaccaataga     1620
aactgggctt gtcgagacag agaagactct tgcgtttctg ataggcacct attggtctta     1680
ctgacatcca ctttgccttt ctctccacag gtgtccactc ccaggttcaa ttacagctct     1740
taagcagccg caagcttgat atcgaattcc tgcagcccgg gggatccact agttctagag     1800
cggccgccac cgcggtggag ctcgaattat cagatcgatt aataactatg ctcaaaaatt     1860 gtgtacctt agcttttaa tttgtaaagg ggttaataag gaatatttga tgtatagtgc       1920
cttgactaga gatcataatc agccatacca catttgtaga ggttttactt gctttaaaaa     1980
acctcccaca cctcccctg aacctgaaac ataaaatgaa tgcaattgtt gttgttaact       2040
tgtttattgc agcttataat ggttacaaat aaagcaatag catcacaaat ttcacaaata     2100
aagcattttt ttcactgcat tctagttgtg gtttgtccaa actcatcaat gtatcttatc     2160
atgtctggat catcagatct gccggtctcc ctatagtgag tcgtattaat ttcgataagc     2220
caggttaacc tgcattaatg aatcggccaa cgcgcgggga gaggcggttt gcgtattggg     2280
cgctcttccg cttcctcgct cactgactcg ctgcgctcgg tcgttcggct gcggcgagcg     2340
gtatcagctc actcaaaggc ggtaatacgg ttatccacag aatcagggga taacgcagga     2400
aagaacatgt gagcaaaagg ccagcaaaag gccaggaacc gtaaaaaggc cgcgttgctg     2460 gcgttttttcc ataggctccg ccccctgac gagcatcaca aaaatcgacg ctcaagtcag     2520
aggtggcgaa acccgacagg actataaaga taccaggcgt ttcccctgg aagctccctc      2580 gtgcgctctc ctgttccgac cctgccgctt accggatacc tgtccgcctt tctccttcg      2640
```

| | |
|---|---:|
| ggaagcgtgg cgctttctca tagctcacgc tgtaggtatc tcagttcggt gtaggtcgtt | 2700 |
| cgctccaagc tgggctgtgt gcacgaaccc cccgttcagc ccgaccgctg cgccttatcc | 2760 |
| ggtaactatc gtcttgagtc caacccggta agacacgact tatcgccact ggcagcagcc | 2820 |
| actggtaaca ggattagcag agcgaggtat gtaggcggtg ctacagagtt cttgaagtgg | 2880 |
| tggcctaact acggctacac tagaagaaca gtatttggta tctgcgctct gctgaagcca | 2940 |
| gttaccttcg gaaaaagagt tggtagctct tgatccggca aacaaaccac cgctggtagc | 3000 |
| ggtggttttt ttgtttgcaa gcagcagatt acgcgcagaa aaaaggatc tcaagaagat | 3060 |
| cctttgatct tttctacggg gtctgacgct cagtggaacg aaaactcacg ttaagggatt | 3120 |
| ttggtcatga gcgcgcctag gcttttgcaa agatcgatca agagacagga tgaggatcgt | 3180 |
| ttcgcatgat tgaacaagat ggattgcacg caggttctcc ggccgcttgg gtggagaggc | 3240 |
| tattcggcta tgactgggca caacagacaa tcggctgctc tgatgccgcc gtgttccggc | 3300 |
| tgtcagcgca ggggcgcccg gttcttttg tcaagaccga cctgtccggt gccctgaatg | 3360 |
| aactgcaaga cgaggcagcg cggctatcgt ggctggccac gacgggcgtt ccttgcgcag | 3420 |
| ctgtgctcga cgttgtcact gaagcgggaa gggactggct gctattgggc gaagtgccgg | 3480 |
| ggcaggatct cctgtcatct caccttgctc ctgccgagaa agtatccatc atggctgatg | 3540 |
| caatgcggcg gctgcatacg cttgatccgg ctacctgccc attcgaccac caagcgaaac | 3600 |
| atcgcatcga gcgagcacgt actcggatgg aagccggtct tgtcgatcag gatgatctgg | 3660 |
| acgaagagca tcaggggctc gcgccagccg aactgttcgc caggctcaag gcgagcatgc | 3720 |
| ccgacggcga ggatctcgtc gtgacccatg gcgatgcctg cttgccgaat atcatggtgg | 3780 |
| aaaatggccg cttttctgga ttcatcgact gtggccggct gggtgtggcg gaccgctatc | 3840 |
| aggacatagc gttggctacc cgtgatattg ctgaagagct tggcggcgaa tgggctgacc | 3900 |
| gcttcctcgt gctttacggt atcgccgctc ccgattcgca gcgcatcgcc ttctatcgcc | 3960 |
| ttcttgacga gttcttctga gcgggactct ggggttcgaa atgaccgacc aagcgacgcc | 4020 |
| caacctgcca tcacgagatt tcgattccac cgccgccttc tatgaaaggt tgggcttcgg | 4080 |
| aatcgttttc cgggacgccg gctggatgat cctccagcgc ggggatctca tgctggagtt | 4140 |
| cttcgcccac cctaggcgcg ctcatgagcg gatacatatt tgaatgtatt tagaaaaata | 4200 |
| aacaaatagg ggttccgcgc acatttcccc gaaaagtgcc ac | 4242 |

<210> SEQ ID NO 2
<211> LENGTH: 4242
<212> TYPE: DNA
<213> ORGANISM: Artificial sequence
<220> FEATURE:
<223> OTHER INFORMATION: Nucleotide sequence of plasmid pGCMB75.6

<400> SEQUENCE: 2

| | |
|---|---:|
| tgaccgccca acgaccccg cccattgacg tcaataatga cgtatgttcc catagtaacg | 60 |
| ccaataggga ctttccattg acgtcaatgg gtggagtatt tacggtaaac tgcccacttg | 120 |
| gcagtacatc aagtgtatca tatgccaagt ccgcccccta ttgacgtcaa tgacggtaaa | 180 |
| tggcccgcct ggcattatgc ccagtacatg accttacggg actttcctac ttggcagtac | 240 |
| atctacgtat tagtcatcgc tattaccatg gtgatgcggt tttggcagta catcaatggg | 300 |
| cgtggatagc ggtttgactc acggggattt ccaagtctcc accccattga cgtcaatggg | 360 |
| agtttgtttt ggcaccaaaa tcaacgggac tttccaaaat gtcgtaacaa ctccgcccca | 420 |
| ttgacgcaaa tgggcggtag gcgtgtacgg tgggaggtct atataagcag agctcgttta | 480 |

```
gtgaaccgtc agatcgcctg gagacgccat ccacgctgtt ttgacctcca tagaagacac    540
cgggaccgat ccagcctccc ctcgaagccg atctgataac ggtaccgata agctggcggc    600
cgattaagct acagaagttg gtcgtgaggc actgggcagg taagtatcaa ggttacaaga    660
caggtttaag gagaccaata gaaactgggc ttgtcgagac agagaagact cttgcgtttc    720
tgataggcac ctattggtct tactgacatc cactttgcct ttctctccac aggtgtccac    780
tcccaggttc aattacagct cttaagcagc cgcaagcttg atatcgaatt cctgcagccc    840
gggggatcca ctagttctag agcggccgcc accgcggtgg agctcgaatt atcagatcga    900
ttaataacta tgctcaaaaa ttgtgtacct ttagcttttt aatttgtaaa ggggttaata    960
aggaatattt gatgtatagt gccttgacta gagatcataa tcagccatac cacatttgta   1020
gaggttttac ttgctttaaa aaacctccca cacctccccc tgaacctgaa acataaaatg   1080
aatgcaattg ttgttgttaa cttgtttatt gcagcttata atggttacaa ataaagcaat   1140
agcatcacaa atttcacaaa taaagcattt ttttcactgc attctagttg tggtttgtcc   1200
aaactcatca atgtatctta tcatgtctgg atcatcagat ctgccggtct ccctatagtg   1260
agtcgtatta atttcgataa gccaggttaa cctgcattaa tgaatcggcc aacgcgcggg   1320
gagaggcggt ttgcgtattg ggcgctcttc cgcttcctcg ctcactgact cgctgcgctc   1380
ggtcgttcgg ctgcggcgag cggtatcagc tcactcaaag gcggtaatac ggttatccac   1440
agaatcaggg gataacgcag gaaagaacat gtgagcaaaa ggccagcaaa aggccaggaa   1500
ccgtaaaaag gccgcgttgc tggcgttttt ccataggctc cgcccccctg acgagcatca   1560
caaaaatcga cgctcaagtc agaggtggcg aaacccgaca ggactataaa gataccaggc   1620
gtttccccct ggaagctccc tcgtgcgctc tcctgttccg accctgccgc ttaccggata   1680
cctgtccgcc tttctccctt cgggaagcgt ggcgctttct catagctcac gctgtaggta   1740
tctcagttcg gtgtaggtcg ttcgctccaa gctgggctgt gtgcacgaac cccccgttca   1800
gcccgaccgc tgcgccttat ccggtaacta tcgtcttgag tccaacccgg taagacacga   1860
cttatcgcca ctggcagcag ccactggtaa caggattagc agagcgaggt atgtaggcgg   1920
tgctacagag ttcttgaagt ggtggcctaa ctacggctac actagaagaa cagtatttgg   1980
tatctgcgct ctgctgaagc cagttacctt cggaaaaaga gttggtagct cttgatccgg   2040
caaacaaacc accgctggta gcggtggttt ttttgtttgc aagcagcaga ttacgcgcag   2100
aaaaaaagga tctcaagaag atcctttgat cttttctacg gggtctgacg ctcagtggaa   2160
cgaaaactca cgttaaggga ttttggtcat gggcgcgcct aggcttttgc aaagatcgat   2220
caagagacag gatgaggatc gtttcgcagc ttttcattct gactgcaacg ggcaataagt   2280
ctctgtgtgg attaaaaaaa gagtgtctga tagcagcttc tgaactggtt acctgccgtg   2340
agtaaattaa aattttattg acttaggtca ctaaggcgcc ttgcgctgag gttgcgtcgt   2400
gatatcatca gggcagaccg gttacatccc cctaacaagc tgtataaaga gaaatactat   2460
ctcattggcg ttgcccgcac ctgacagtgc gacgttgggc tgcgtccgtc gaccaacggt   2520
accgaggtaa cagcccaatc tatccatgat ctcggccagg ccgggtcggc cgttatgcag   2580
cccggctcgg gtatgaagcc attaaggagc gacccagcg cgaccgggcg gccggtcacg   2640
ctgcctctgc tgaagcctgc ctgtcactcc ctgcgcggcg tacccgccgt tctcatcgag   2700
taggctccgg atcgcgaccc cggacgggcc ctgggcccag gagcggccta tgacaaatgc   2760
cgggtagcga tccggcattc agcattgact gcgcacggat ccagtccttg caggagcctt   2820
atgccgaccg tagcaaaaaa tgagcccgag ccgatcgcga gttgtgatcc ggtcccgccg   2880
```

```
attgccggtc gcgatgacgg tcctgtgtaa gcgttatcgt taccaattgt ttaagaagta      2940
tatacgctac gaggtacttg ataacttctg cgtagcatac atgaggtttt gtataaaaat      3000
ggcgggcgat atcaacgcag tgtcagaaat ccgaaacagt ctgcgggact ctggggttcg      3060
aaatgaccga ccaagcgacg cccaacctgc catcacgaga tttcgattcc accgccgcct      3120
tctatgaaag gttgggcttc ggaatcgttt tccgggacgc cggctggatg atcctccagc      3180
gcggggatct catgctggag ttcttcgccc accctaggcg cgctcatgag cggatacata      3240
tttgaatgta tttagaaaaa taaacaaata ggggttccgc gcacatttcc ccgaaaagtg      3300
ccacctaaat tgtaagcgtt aatattttgt taaaattcgc gttaaatttt tgttaaatca      3360
gctcattttt taaccaatag gccgaaatcg gcaaaatccc ttataaatca aagaataga       3420
ccgagatagg gttgagtgtt gttccagttt ggaacaagag tccactatta agaacgtgg       3480
actccaacgt caaagggcga aaaccgtct atcagggcga tggcccacta cgtgaaccat       3540
caccctaatc aagttttttg gggtcgaggt gccgtaaagc actaaatcgg aaccctaaag      3600
ggagccccg atttagagct tgacgggga agccggcgaa cgtggcgaga aaggaaggga        3660
agaaagcgaa aggagcgggc gctagggcgc tggcaagtgt agcggtcacg ctgcgcgtaa      3720
ccaccacacc cgccgcgctt aatgcgccgc tacagggcgc gtcccattcg ccattcaggc      3780
tgcgcaactg ttgggaaggg cgatcggtgc gggcctcttc gctattacgc cagctggcga      3840
aagggggatg tgctgcaagg cgattaagtt gggtaacgcc agggttttcc cagtcacgac      3900
gttgtaaaac gacggccagt gagcgcgcgt aatacgactc actatagggc gaattgggta      3960
ccgggccccc cctcgagcag gatctataca ttgaatcaat attggcaatt agccatatta      4020
gtcattggtt atatagcata aatcaatatt ggctattggc cattgcatac gttgtatcta      4080
tatcataata tgtacattta tattggctca tgtccaatat gaccgccatg ttgacattga      4140
ttattgacta gttattaata gtaatcaatt acgggtcat tagttcatag cccatatatg       4200
gagttccgcg ttacataact tacggtaaat ggcccgcctg gc                         4242
```

<210> SEQ ID NO 3
<211> LENGTH: 4242
<212> TYPE: DNA
<213> ORGANISM: Artificial sequence
<220> FEATURE:
<223> OTHER INFORMATION: Nucelotide sequence of plasmid pLacZMB75.6

<400> SEQUENCE: 3

```
tgaccgccca acgaccccg cccattgacg tcaataatga cgtatgttcc catagtaacg         60
ccaataggga ctttccattg acgtcaatgg gtggagtatt tacggtaaac tgcccacttg        120
gcagtacatc aagtgtatca tatgccaagt ccgcccccta ttgacgtcaa tgacggtaaa        180
tggcccgcct ggcattatgc ccagtacatg accttacggg actttcctac ttggcagtac        240
atctacgtat tagtcatcgc tattaccatg gtgatgcggt tttggcagta catcaatggg        300
cgtggatagc ggtttgactc acggggattt ccaagtctcc accccattga cgtcaatggg        360
agtttgtttt ggcaccaaaa tcaacgggac tttccaaaat gtcgtaacaa ctccgcccca        420
ttgacgcaaa tgggcggtag gcgtgtacgg tgggaggtct atataagcag agctcgttta       480
gtgaaccgtc agatcgcctg gagacgccat ccacgctgtt tgacctcca tagaagacac         540
cgggaccgat ccagcctccc ctcgaagccg atctgataac ggtaccgata agctggcggc        600
cgattaagct acagaagttg gtcgtgaggc actgggcagg taagtatcaa ggttacaaga       660
caggtttaag gagaccaata gaaactgggc ttgtcgagac agagaagact cttgcgtttc        720
```

```
tgataggcac ctattggtct tactgacatc cactttgcct ttctctccac aggtgtccac      780
tcccaggttc aattacagct cttaagcagc cgccaaaaca aaattcctca aaaatcatca      840
tcgaatgaat ggtgaaataa tttccctgaa taactgtagt gttttcaggg cgcggcataa      900
taattaacta tgctcaaaaa ttgtgtacct ttagcttttt aatttgtaaa ggggttaata      960
aggaatattt gatgtatagt gccttgacta gagatcataa tcagccatac cacatttgta     1020
gaggttttac ttgctttaaa aaacctccca cacctcccccc tgaacctgaa acataaaatg    1080
aatgcaattg ttgttgttaa cttgtttatt gcagcttata atggttacaa ataaagcaat     1140
agcatcacaa atttcacaaa taaagcattt ttttcactgc attctagttg tggtttgtcc     1200
aaactcatca atgtatctta tcatgtctgg atcatcagat ctgccggtct ccctatagtg     1260
agtcgtatta atttcgataa gccaggttaa cctgcattaa tgaatcggcc aacgcgcggg     1320
gagaggcggt ttgcgtattg ggcgctcttc cgcttcctcg ctcactgact cgctgcgctc     1380
ggtcgttcgg ctgcggcgag cggtatcagc tcactcaaag gcggtaatac ggttatccac     1440
agaatcaggg gataacgcag gaaagaacat gtgagcaaaa ggccagcaaa aggccaggaa     1500
ccgtaaaaag gccgcgttgc tggcgttttt ccataggctc cgcccccctg acgagcatca     1560
caaaaatcga cgctcaagtc agaggtggcg aaacccgaca ggactataaa gataccaggc     1620
gtttccccct ggaagctccc tcgtgcgctc tcctgttccg accctgccgc ttaccggata     1680
cctgtccgcc tttctccctt cgggaagcgt ggcgctttct catagctcac gctgtaggta     1740
tctcagttcg gtgtaggtcg ttcgctccaa gctgggctgt gtgcacgaac cccccgttca     1800
gcccgaccgc tgcgccttat ccggtaacta tcgtcttgag tccaacccgg taagacacga     1860
cttatcgcca ctggcagcag ccactggtaa caggattagc agagcgaggt atgtaggcgg     1920
tgctacagag ttcttgaagt ggtggcctaa ctacggctac actagaagaa cagtatttgg     1980
tatctgcgct ctgctgaagc cagttacctt cggaaaaaga gttggtagct cttgatccgg     2040
caaacaaacc accgctggta gcggtggttt ttttgtttgc aagcagcaga ttacgcgcag     2100
aaaaaaagga tctcaagaag atcctttgat cttttctacg gggtctgacg ctcagtggaa     2160
cgaaaactca cgttaaggga ttttggtcat gggcgcgcct aggcttttgc aaagatcgat     2220
caagagacag gatgaggatc gtttcgcagc ttttcattct gactgcaacg ggcaataagt     2280
ctctgtgtgg attaaaaaaa gagtgtctga tagcagcttc tgaactggtt acctgccgtg     2340
agtaaattaa aattttattg acttaggtca ctaaggcgcc ttgcgctgag gttgcgtcgt     2400
gatatcatca gggcagaccg gttacatccc cctaacaagc tgtataaaga gaaatactat     2460
ctcattggcg ttgcccgcac ctgacagtgc gacgttgggc tgcgtccgtc gaccaacggt     2520
accgaggtaa cagcccaatc tatccatgat ctcggccagg ccgggtcggc cgttatgcag     2580
cccggctcgg gtatgaagcc attaaggagc cgacccagcg cgaccgggcg gccggtcacg     2640
ctgcctctgc tgaagcctgc ctgtcactcc ctgcgcggcg tacccgccgt tctcatcgag     2700
taggctccgg atcgcgaccc cggacgggcc ctgggcccag gagcggccta tgacaaatgc     2760
cgggtagcga tccggcattc agcattgact gcgcacggat ccagtccttg caggagcctt     2820
atgccgaccg tagcaaaaaa tgagcccgag ccgatcgcga gttgtgatcc ggtcccgccg     2880
attgccggtc gcgatgacgg tcctgtgtaa gcgttatcgt taccaattgt ttaagaagta     2940
tatacgctac gaggtacttg ataacttctg cgtagcatac atgaggtttt gtataaaaat     3000
ggcgggcgat atcaacgcag tgtcagaaat ccgaaacagt ctgcgggact ctggggttcg     3060
aaatgaccga ccaagcgacg cccaacctgc catcacgaga tttcgattcc accgccgcct     3120
```

```
tctatgaaag gttgggcttc ggaatcgttt tccgggacgc cggctggatg atcctccagc   3180
gcggggatct catgctggag ttcttcgccc accctaggcg cgctcatgag cggatacata   3240
tttgaatgta tttagaaaaa taaacaaata ggggttccgc gcacatttcc ccgaaaagtg   3300
ccacctaaat tgtaagcgtt aatattttgt taaaattcgc gttaaatttt tgttaaatca   3360
gctcattttt taaccaatag gccgaaatcg gcaaaatccc ttataaatca aaagaataga   3420
ccgagatagg gttgagtgtt gttccagttt ggaacaagag tccactatta agaacgtgg   3480
actccaacgt caaagggcga aaaccgtct atcagggcga tggcccacta cgtgaaccat   3540
caccctaatc aagtttttg gggtcgaggt gccgtaaagc actaaatcgg aaccctaaag   3600
ggagcccccg atttagagct tgacggggaa agccggcgaa cgtggcgaga aaggaaggga   3660
agaaagcgaa aggagcgggc gctagggcgc tggcaagtgt agcggtcacg ctgcgcgtaa   3720
ccaccacacc cgccgcgctt aatgcgccgc tacagggcgc gtcccattcg ccattcaggc   3780
tgcgcaactg ttgggaaggg cgatcggtgc gggcctcttc gctattacgc cagctggcga   3840
aagggggatg tgctgcaagg cgattaagtt gggtaacgcc agggttttcc cagtcacgac   3900
gttgtaaaac gacggccagt gagcgcgcgt aatacgactc actatagggc gaattgggta   3960
ccgggccccc cctcgaggtc gacggtatcg ataagcttga tatcgaattc ctgcagcccg   4020
ggggatccac tagttctaga gcggccgcca ccgcggtgga gctccagctt ttgttcccctt   4080
tagtgagggt taattgcgcg cttggcgtaa tcatggtcat agctgtttcc tgtgtgaaat   4140
tgttatccgc tcacaattcc acacaacata cgagccggaa gcataaagtg taaagcctgg   4200
ggtgcctaat gagtgagcta actcacatta attgcgttgc gc                      4242
```

<210> SEQ ID NO 4
<211> LENGTH: 4242
<212> TYPE: DNA
<213> ORGANISM: Artificial sequence
<220> FEATURE:
<223> OTHER INFORMATION: Nucleotide sequence of plasmid pMB75.6_AscI

<400> SEQUENCE: 4

```
tgaccgccca acgaccccg cccattgacg tcaataatga cgtatgttcc catagtaacg    60
ccaatagggaa ctttccattg acgtcaatgg gtggagtatt tacggtaaac tgcccacttg   120
gcagtacatc aagtgtatca tatgccaagt ccgcccccta ttgacgtcaa tgacggtaaa   180
tggcccgcct ggcattatgc ccagtacatg accttacggg actttcctac ttggcagtac   240
atctacgtat tagtcatcgc tattaccatg gtgatgcggt tttggcagta catcaatggg   300
cgtggatagc ggtttgactc acggggattt ccaagtctcc accccattga cgtcaatggg   360
agtttgtttt ggcaccaaaa tcaacgggac tttccaaaat gtcgtaacaa ctccgcccca   420
ttgacgcaaa tgggcggtag gcgtgtacgg tgggaggtct atataagcag agctcgttta   480
gtgaaccgtc agatcgcctg gagacgccat ccacgctgtt ttgacctcca tagaagacac   540
cgggaccgat ccagcctccc ctcgaagccg atctgataac ggtaccgata agctggcggc   600
cgattaagct acagaagttg gtcgtgaggc actgggcagg taagtatcaa ggttacaaga   660
caggtttaag gagaccaata gaaactgggc ttgtcgagac agagaagact cttgcgtttc   720
tgataggcac ctattggtct tactgacatc cactttgcct ttctctccac aggtgtccac   780
tcccaggttc aattacagct cttaagcagc gcaagcttg atatcgaatt cctgcagccc   840
ggggatcca ctagttctag agcggccgcc accgcggtgg agctcgaatt atcagatcga   900
ttaataacta tgctcaaaaa ttgtgtacct ttagcttttt aatttgtaaa ggggttaata   960
```

```
aggaatattt tgatgtatagt gccttgacta gagatcataa tcagccatac cacatttgta    1020
gaggttttac ttgctttaaa aaacctccca caactcccccc tgaacctgaa acataaaatg    1080
aatgcaattg ttgttgttaa cttgtttatt gcagcttata atggttacaa ataaagcaat    1140
agcatcacaa atttcacaaa taaagcattt ttttcactgc attctagttg tggtttgtcc    1200
aaactcatca atgtatctta tcatgtctgg atcatcagat ctgccggtct ccctatagtg    1260
agtcgtatta atttcgataa gccaggttaa cctgcattaa tgaatcggcc aacgcgcggg    1320
gagaggcggt ttgcgtattg ggcgctcttc cgcttcctcg ctcactgact cgctgcgctc    1380
ggtcgttcgg ctgcggcgag cggtatcagc tcactcaaag gcggtaatac ggttatccac    1440
agaatcaggg gataacgcag gaaagaacat gtgagcaaaa ggccagcaaa aggccaggaa    1500
ccgtaaaaag gccgcgttgc tggcgttttt ccataggctc cgcccccctg acgagcatca    1560
caaaaatcga cgctcaagtc agaggtggcg aaacccgaca ggactataaa gataccaggc    1620
gtttccccct ggaagctccc tcgtgcgctc tcctgttccg accctgccgc ttaccggata    1680
cctgtccgcc tttctccctt cgggaagcgt ggcgctttct catagctcac gctgtaggta    1740
tctcagttcg gtgtaggtcg ttcgctccaa gctgggctgt gtgcacgaac cccccgttca    1800
gcccgaccgc tgcgccttat ccggtaacta tcgtcttgag tccaacccgg taagacacga    1860
cttatcgcca ctggcagcag ccactggtaa caggattagc agagcgaggt atgtaggcgg    1920
tgctacagag ttcttgaagt ggtggcctaa ctacggctac actagaagaa cagtatttgg    1980
tatctgcgct ctgctgaagc cagttacctt cggaaaaaga gttggtagct cttgatccgg    2040
caaacaaacc accgctggta gcggtggttt ttttgtttgc aagcagcaga ttacgcgcag    2100
aaaaaaagga tctcaagaag atcctttgat cttttctacg gggtctgacg ctcagtggaa    2160
cgaaaactca cgttaaggga ttttggtcat gggcgcgcct aggcttttgc aaagatcgat    2220
caagagacag gatgaggatc gtttcgcatg attgaacaag atggattgca cgcaggttct    2280
ccggccgctt gggtggagag gctattcggc tatgactggg cacaacagac aatcggctgc    2340
tctgatgccg ccgtgttccg gctgtcagcg caggggcgcc cggttctttt tgtcaagacc    2400
gacctgtccg gtgccctgaa tgaactgcaa gacgaggcag cgcggctatc gtggctggcc    2460
acgacgggcg ttccttgcgc agctgtgctc gacgttgtca ctgaagcggg aagggactgg    2520
ctgctattgg gcgaagtgcc ggggcaggat ctcctgtcat ctcaccttgc tcctgccgag    2580
aaagtatcca tcatggctga tgcaatgcgg cggctgcata cgcttgatcc ggctacctgc    2640
ccattcgacc accaagcgaa acatcgcatc gagcgagcac gtactcggat ggaagccggt    2700
cttgtcgatc aggatgatct ggacgaagag catcaggggc tcgcgccagc cgaactgttc    2760
gccaggctca aggcgagcat gcccgacggc gaggatctcg tcgtgaccca tggcgatgcc    2820
tgcttgccga atatcatggt ggaaaatggc cgcttttctg gattcatcga ctgtggccgg    2880
ctgggtgtgg cggaccgcta tcaggacata gcgttggcta cccgtgatat tgctgaagag    2940
cttggcggcg aatgggctga ccgcttcctc gtgctttacg gtatcgccgc tcccgattcg    3000
cagcgcatcg ccttctatcg ccttcttgac gagttcttct gagcgggact ctggggttcg    3060
aaatgaccga ccaagcgacg cccaacctgc catcacgaga tttcgattcc accgccgcct    3120
tctatgaaag gttgggcttc ggaatcgttt tccgggacgc cggctggatg atcctccagc    3180
gcggggatct catgctggag ttcttcgccc accctaggcg cgctcatgag cggatacata    3240
tttgaatgta tttagaaaaa taaacaaata ggggttccgc gcacatttcc ccgaaaagtg    3300
ccacctaaat tgtaagcgtt aatattttgt taaaattcgc gttaaatttt tgttaaatca    3360
```

```
gctcattttt taaccaatag gccgaaatcg gcaaaatccc ttataaatca aaagaataga    3420
ccgagatagg gttgagtgtt gttccagttt ggaacaagag tccactatta aagaacgtgg    3480
actccaacgt caaagggcga aaaccgtct atcagggcga tggcccacta cgtgaaccat    3540
caccctaatc aagttttttg gggtcgaggt gccgtaaagc actaaatcgg aaccctaaag    3600
ggagcccccg atttagagct tgacggggaa agccggcgaa cgtggcgaga aaggaaggga    3660
agaaagcgaa aggagcgggc gctagggcgc tggcaagtgt agcggtcacg ctgcgcgtaa    3720
ccaccacacc cgccgcgctt aatgcgccgc tacagggcgc gtcccattcg ccattcaggc    3780
tgcgcaactg ttgggaaggg cgatcggtgc gggcctcttc gctattacgc cagctggcga    3840 aaggggatg tgctgcaagg cgattaagtt gggtaacgcc agggttttcc cagtcacgac    3900
gttgtaaaac gacggccagt gagcgcgcgt aatacgactc actatagggc gaattggta    3960 ccgggccccc cctcgagcag gatctataca ttgaatcaat attggcaatt agccatatta    4020
gtcattggtt atatagcata aatcaatatt ggctattggc cattgcatac gttgtatcta    4080
tatcataata tgtacattta tattggctca tgtccaatat gaccgccatg ttgacattga    4140
ttattgacta gttattaata gtaatcaatt acggggtcat tagttcatag cccatatatg    4200
gagttccgcg ttacataact tacggtaaat ggcccgcctg gc                       4242
```

INCREASED FERTILITY IN BOVINE SPECIES

CROSS-REFERENCE TO RELATED APPLICATIONS

This application is a National Stage entry of International Application No. PCT/US2017/043662, filed Jul. 25, 2017, which claims priority to U.S. Provisional Patent Application No. 62/366,772, filed Jul. 26, 2016.

REFERENCE TO SEQUENCE LISTING SUBMITTED AS A COMPLIANT ASCII TEXT FILE (.txt)

The instant application contains a substitute Sequence Listing which has been submitted electronically in ASCII format and is hereby incorporated by reference in its entirety. Pursuant to the EFS-Web legal framework and 37 C.F.R. §§ 1.821-825 (see MPEP § 2442.03(a)), a Substitute Sequence Listing in the form of an ASCII-compliant text file (entitled 2920951-141000_Substitute_Sequence_Listing_ST25.txt created on 24 Sep. 2020, and 23,038 bytes in size) is submitted concurrently with the instant application, and the entire contents of the Substitute Sequence listing is incorporated herein by reference.

BACKGROUND

Field of the Invention

The present invention relates to a compositions and methods for immunomodulation in cows. In particular, the present invention includes compositions and methods which are effective for increasing first service conception rate in cows.

Description of Related Art

The highest morbidity and mortality in dairy cattle occurs in the peripartum period. It has been shown that immune function is compromised around calving, with reduced white cell count and reduced white cell function as demonstrated via myeloperoxidase and phagocytosis assays. If immune function could be enhanced around calving, then reproductive outcomes, which may be sensitive to immune function, could be improved.

Dairy cattle fertility is declining on an international scale due to multiple factors including increasing herd size, reduced oestrus detection sensitivity and specificity, declining body condition score at calving and increased rate of body condition score loss postpartum. McDougall, J. Reproduction and Development 52, 185-194 (2006). High levels of reproductive performance are necessary to maintain optimum herd health and productivity. There is a need in the art for compositions and methods capable of increasing reproductive abilities of cows and heifers.

SUMMARY

The present invention relates to immunomodulator compositions for increasing conception rates in cows and heifers. In some embodiments, the immunomodulator composition may comprise a cationic liposome delivery vehicle and an isolated bacterially-derived nucleic acid molecule that does not code for an immunogen for increasing conception rate in cows and heifers.

In some embodiments, the nucleic acid molecule comprises at least one immunostimulatory CpG motif and at least one non-immunostimulatory CpG motif. In further embodiments, the nucleic acid molecule has at least 80% sequence homology with the sequence of SEQ ID NO: 1 SEQ ID NO: 2, SEQ ID NO: 3, or SEQ ID NO: 4. In some embodiments, the nucleic acid molecule comprises SEQ ID NO: 1. In other embodiments, the nucleic acid molecule comprises SEQ ID NO: 2. In other embodiments, the nucleic acid molecule comprises SEQ ID NO: 3. In other embodiments, the nucleic acid molecule comprises SEQ ID NO: 4.

In some embodiments, the liposome delivery vehicle comprises lipids selected from the group consisting of multilamellar vesicle lipids and extruded lipids. In further embodiments, the liposome delivery vehicle comprises pairs of lipids selected from the group consisting of N-[1-(2,3-dioleyloxy)propyl]-N,N,N-trimethylanimonium chloride (DOTMA) and cholesterol; N-[1-(2,3-dioleoyloxy)propyl] N,N,N-trimethylammonium chloride (DOTAP) and cholesterol; 1-[2-(oleoyloxy)ethyl]-2-oleyl-3-(2-hydroxyethyl) imidazolinium chloride (DOTIM) and cholesterol; and dimethyldioctadecylammonium bromide (DDAB) and cholesterol.

In some embodiments, the immunomodulator composition further comprises a biological agent. In further embodiments, the biological agent is selected from the group consisting of immune enhancer proteins, immunogens, vaccines, antimicrobials or any combination thereof. In some embodiments, the immunomodulator composition further comprises a pharmaceutically acceptable carrier.

In some embodiments, the immunomodular composition is for administration and selected from the group consisting of intravenously, intramuscularly, intradermal, intraperitoneal, subcutaneously, by spray-aerosol, orally, intraocularly, intracheally, intrauterine, intravaginal, and intranasal.

In some embodiments, the conception rate in cows increases relative to the conception rate in a control population.

In some embodiments, the conception rate in non-cycling cows increases relative to the conception rate in a control population.

In some embodiments, the first service conception rate in cows increases relative to the first service conception rate in a control population.

In some embodiments, the first service conception rate in non-cycling cows increases relative to the first service conception rate in a control population.

In some embodiments, the conception rate in cows increases relative to the first service conception rate in a control population as measured by a p-value of ≤0.05.

In some embodiments, the conception rate in non-cycling cows increases relative to the conception rate in a control population as measured by a p-value of ≤0.05.

In some embodiments, the first service conception rate in cows increases relative to the first service conception rate in a control population as measured by a p-value of ≤0.05.

In some embodiments, the first service conception rate in non-cycling cows increases relative to the first service conception rate in a control population as measured by a p-value of ≤0.05.

The present invention also relates to methods of increasing the conception rate in cows comprising administering to the cows an effective amount of an immunomodulator composition. In some embodiments, the immunomodulator composition may comprise a cationic liposome delivery vehicle and a nucleic acid molecule that does not code for an immunogen.

The present invention also relates to methods of increasing the conception rate in cows comprising administering to the cows an effective amount of an immunomodulator composition. In some embodiments, the immunomodulator composition may comprise a cationic liposome delivery vehicle and an isolated bacterially-derived nucleic acid molecule that does not code for an immunogen.

The present invention also relates to methods of increasing the conception rate in non-cycling cows comprising administering to the cows an effective amount of an immunomodulator composition. In some embodiments, the immunomodulator composition may comprise a cationic liposome delivery vehicle and a nucleic acid molecule that does not code for an immunogen.

The present invention also relates to methods of increasing the conception rate in non-cycling cows comprising administering to the cows an effective amount of an immunomodulator composition. In some embodiments, the immunomodulator composition may comprise a cationic liposome delivery vehicle and an isolated bacterially-derived nucleic acid molecule that does not code for an immunogen.

The present invention also relates to methods of increasing the first service conception rate in cows comprising administering to the cows an effective amount of an immunomodulator composition. In some embodiments, the immunomodulator composition may comprise a cationic liposome delivery vehicle and a nucleic acid molecule that does not code for an immunogen.

The present invention also relates to methods of increasing the first service conception rate in cows comprising administering to the cows an effective amount of an immunomodulator composition. In some embodiments, the immunomodulator composition may comprise a cationic liposome delivery vehicle and an isolated bacterially-derived nucleic acid molecule that does not code for an immunogen.

The present invention also relates to methods of increasing the first service conception rate in non-cycling cows comprising administering to the cows an effective amount of an immunomodulator composition. In some embodiments, the immunomodulator composition may comprise a cationic liposome delivery vehicle and a nucleic acid molecule that does not code for an immunogen.

The present invention also relates to methods of increasing the first service conception rate in non-cycling cows comprising administering to the cows an effective amount of an immunomodulator composition. In some embodiments, the immunomodulator composition may comprise a cationic liposome delivery vehicle and an isolated bacterially-derived nucleic acid molecule that does not code for an immunogen.

In some embodiments, the nucleic acid molecule comprises at least one immunostimulatory CpG motif and at least one non-immunostimulatory CpG motif. In further embodiments, the nucleic acid molecule has at least 80% sequence homology with the sequence of SEQ ID NO: 1, SEQ ID NO: 2, SEQ ID NO: 3, or SEQ ID NO: 4. In some embodiments, the nucleic acid molecule comprises SEQ ID NO: 1. In other embodiments, the nucleic acid molecule comprises SEQ ID NO: 2. In other embodiments, the nucleic acid molecule comprises SEQ ID NO: 3. In other embodiments, the nucleic acid molecule comprises SEQ ID NO: 4.

In some embodiments, the liposome delivery vehicle comprises lipids selected from the group consisting of multilamellar vesicle lipids and extruded lipids. In further embodiments, the liposome delivery vehicle comprises pairs of lipids selected from the group consisting of N-[1-(2,3-dioleyloxy)propyl]-N,N,N-trimethylanimonium chloride (DOTMA) and cholesterol; N-[1-(2,3-dioleoyloxy)propyl] N,N,N-trimethylammonium chloride (DOTAP) and cholesterol; 1-[2-(oleoyloxy)ethyl]-2-oleyl-3-(2-hydroxyethyl) imidazolinium chloride (DOTIM) and cholesterol; and dimethyldioctadecylammonium bromide (DDAB) and cholesterol.

In some embodiments, the immunomodulator composition further comprises a biological agent. In further embodiments, the biological agent is selected from the group consisting of immune enhancer proteins, immunogens, vaccines, antimicrobials or any combination thereof. In some embodiments, the immunomodulator composition further comprises a pharmaceutically acceptable carrier.

In some embodiments, the immunomodular composition is for administration and selected from the group consisting of intravenously, intramuscularly, intradermal, intraperitoneal, subcutaneously, by spray-aerosol, orally, intraocularly, intracheally, and intranasal.

DETAILED DESCRIPTION OF A PREFERRED EMBODIMENT

Figure 1:
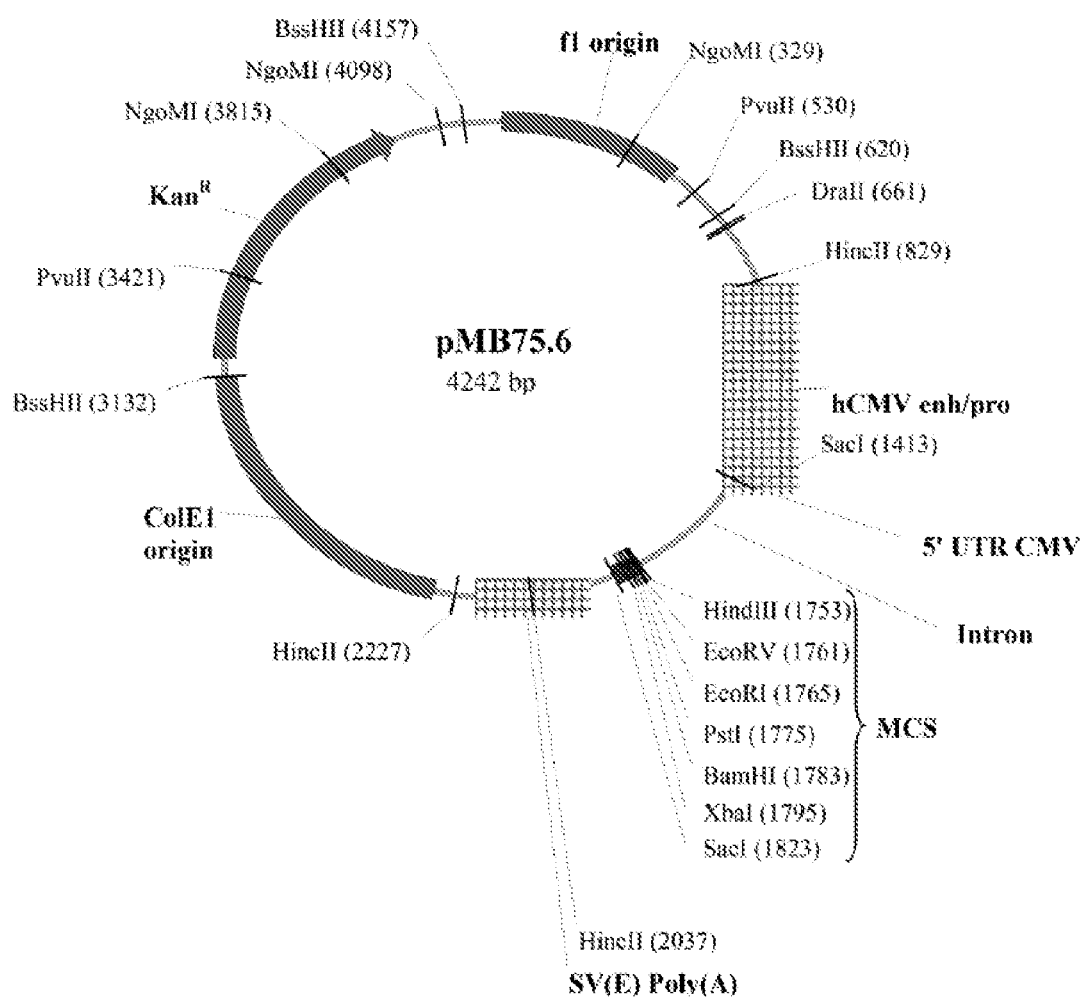
FIG. 1 shows a map of the pMB75.6 plasmid (SEQ ID NO: 1)
Figure 2:
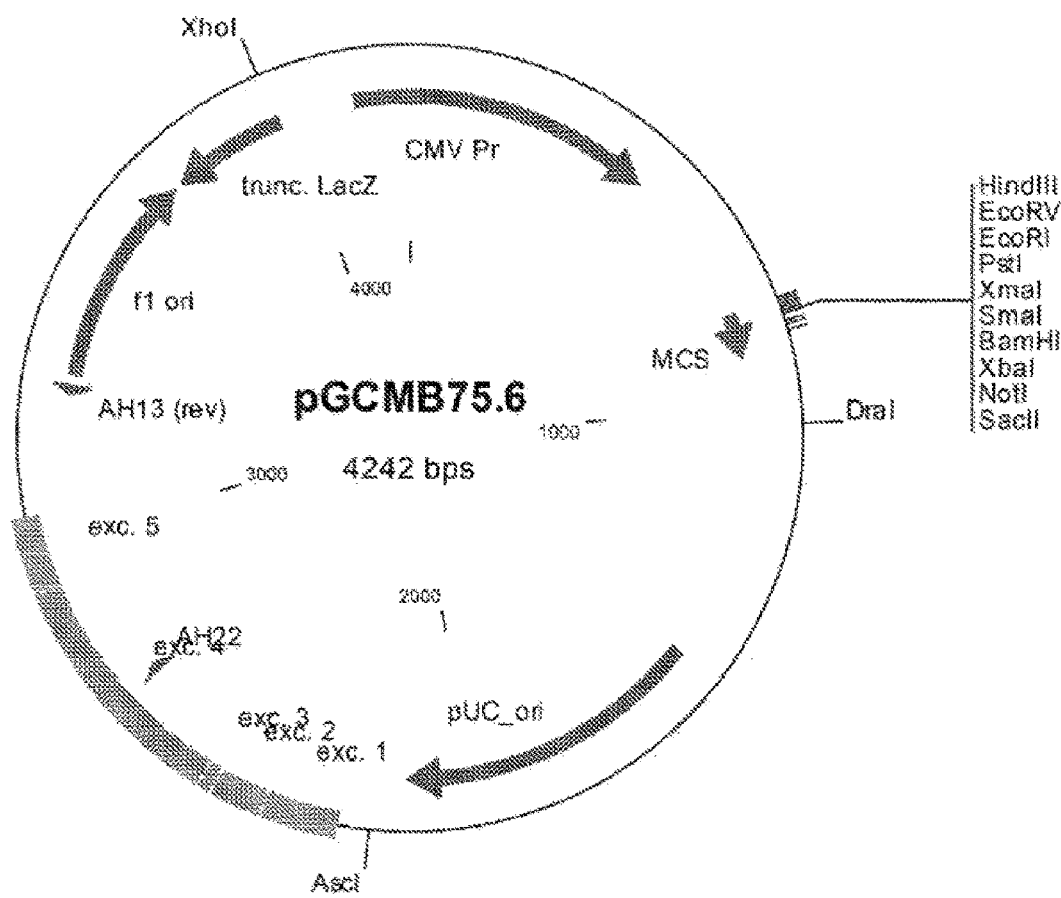
FIG. 2 shows a map of the pGCMB75.6 plasmid (SEQ ID NO: 2)

In accordance with the present invention, immunomodulator compositions and methods of use thereof for increasing the conception rate in cows. The immunomodulator composition includes a cationic liposome delivery vehicle and an isolated bacterially-derived nucleic acid molecule that does not code for an immunogen. The compositions and methods of using the immunomodulator compositions are discussed in more detail below.

I. Composition

Compositions useful in this invention, such as those described herein, are generally able to be used as a prophylactic therapy, metaphylactic therapy, or treatment therapy for infectious diseases. Such compositions are referred to herein as immunomodulator compositions. The immunomodulator compositions include at least an immunostimulatory plasmid or immunostimulatory DNA sequence, capable of increasing the conception rate in cows. In some aspects, the immunomodulator compositions may also include a liposome delivery vehicle.

A. Nucleic Acids

In some aspects the present invention relates to nucleic acid molecules useful for increasing the conception rate in cows. The nucleic acid molecules described herein may be included in an immunostimulatory plasmid, as linear double stranded or single stranded DNA, amino acid sequence, ribonucleic acid (RNA), or combinations thereof. In some aspects, the present invention relates to nucleic acid molecules, vectors, and host cells (in vitro, in vivo, or ex vivo) which contain the immunostimulatory plasmid or immunostimulatory DNA sequence.

The nucleic acid molecules described herein are enriched in CpG motifs. Such CpG motifs may induce immune stimulation via specific Toll-like receptors, such as TLR9 and TLR21. In addition the nucleic acid molecules described herein also contain non-CpG immunostimulatory motifs. In some aspects, the nucleic acid molecules contain about 2-20% CpG motifs over the frequency of CpG motifs expected in random nucleic acid sequences. In some aspects, the nucleic acid molecules contain about 3, 4, 5, 6, 7, 8, 9, 10, 11, 12, 13, 14, 15, 16, 17, 18, 19, 20, 25, 30, 35, 40%, or more CpG motifs over the frequency of CpG motifs expected in random nucleic acid sequences. In some aspects, the nucleic acid molecules contain about 10% CpG motifs over the frequency of CpG motifs expected in random nucleic acid sequences. In some aspects, compared to vertebrate DNA, an enrichment of CpG motifs of more than 10-fold is observed. In some aspects, the nucleic acid molecules contain about 2 to 50 fold, or more CpG motifs compared to vertebrate DNA. In some aspects, the nucleic acid molecules contain about 3, 4, 5, 6, 7, 8, 9, 10, 11, 12, 13, 14, 15, 16, 17, 18, 19, 20, 25, 30, 35, 40, 45, 50, 55 fold or more CpG motifs compared to vertebrate DNA.

In some aspects, the present invention relates to immunostimulatory plasmids, or DNA sequences, that do comprise an antibiotic resistance gene. For example, the pMB75.6 plasmid described herein comprises an the antibiotic resistance gene kanamycin. The sequence of pMG75.6 is provided in Table 1 as SEQ ID NO: 1.

In some aspects, the present invention relates to immunostimulatory plasmids, or DNA sequences, that do not comprise an antibiotic resistance gene. The plasmids may be devoid of any selectable or screenable marker genes. For example, the pGCMB75.6 plasmid described herein does not comprise any full-length or functional selectable or screenable marker genes. The sequence of pGCMB75.6 is provided in Table 1 as SEQ ID NO: 2.

In some aspects, the immunostimulatory plasmids described herein preferably do not comprise a nucleic acid sequence coding for a full-length or functional selectable or screenable marker. In some aspects, the immunostimulatory plasmids do not comprise an antibiotic resistance gene. For example, the plasmids do not comprise a kanamycin resistance gene. In some aspects, the plasmids described herein preferably do not encode an immunogen.

Figure 3:
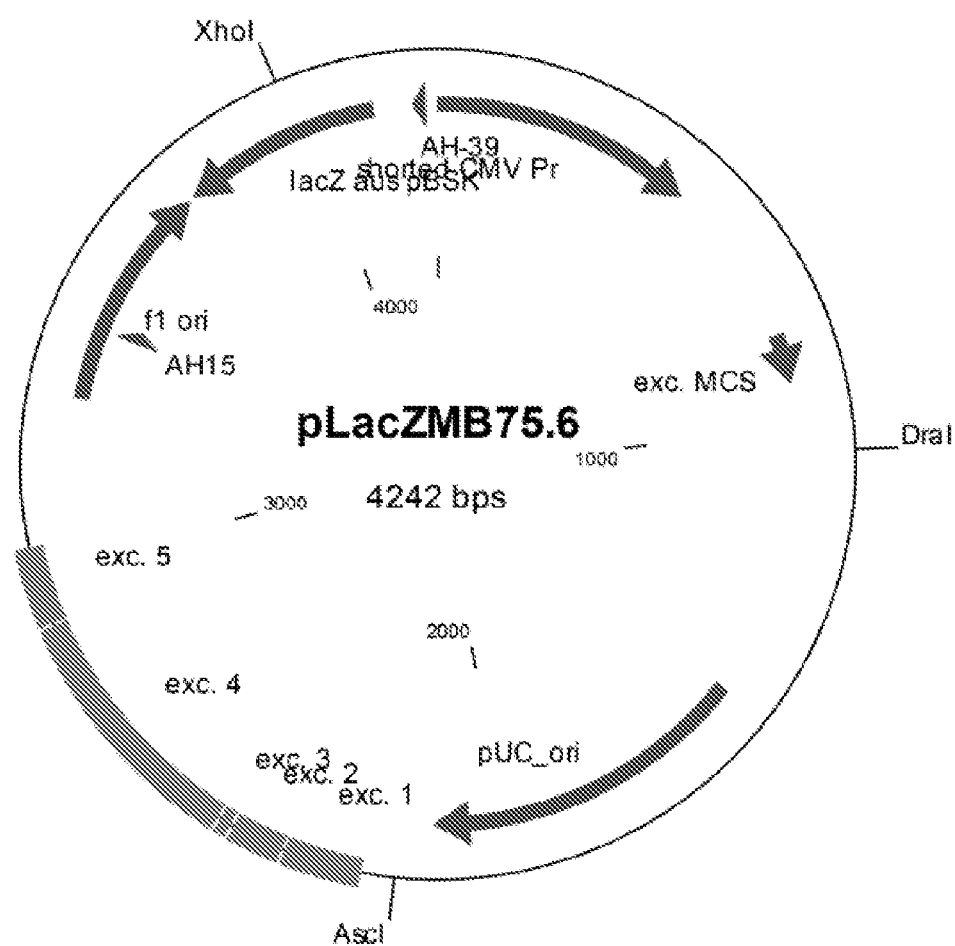
FIG. 3. Shows a map of the pLacZMB75.6 plasmid (SEQ ID NO: 3)

In some aspects, the immunostimulatory plasmids may comprise a nucleic acid sequence coding for a selectable or screenable marker gene that is not an antibiotic resistance gene. For example, the pLacZMB75.6 plasmid described herein comprises a LacZ gene as a screenable marker. A map of pLacZMB75.6 is provided in FIG. 3 and the nucleotide sequence of pLacZMB75.6 is provided in Table 1 as SEQ ID NO: 3. As shown in FIG. 3, pLacZMB75.6 is similar to pGCMB75.6, but contains a LacZ screenable marker.

It will be appreciated that the nucleotide sequences of the pMB75.6, pGCMB75.6 or pLacZMB75.6 plasmids may be varied to a certain extent without significantly adversely affecting their immunostimulatory properties. In some aspects, the present invention relates to an immunostimulatory plasmid comprising a nucleic acid sequence having at least 80% sequence identity with the sequence of pMB75.6 (SEQ ID NO: 1). The immunostimulatory plasmid preferably comprises a nucleic acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of pMB75.6 (SEQ ID NO: 1). In some aspects, the immunostimulatory plasmid more preferably comprises the sequence of pMB75.6 (SEQ ID NO: 1).

In some aspects, the present invention relates to an immunostimulatory plasmid comprising a nucleic acid sequence having at least 80% sequence identity with the sequence of pGCMB75.6 (SEQ ID NO: 2). The immunostimulatory plasmid preferably comprises a nucleic acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of pGCMB75.6 (SEQ ID NO: 2). In some aspects, the immunostimulatory plasmid more preferably comprises the sequence of pGCMB75.6 (SEQ ID NO: 2).

In some aspects, the present invention relates to an immunostimulatory plasmid consisting of a nucleic acid sequence having at least 80% sequence identity with the sequence of pMB75.6 (SEQ ID NO: 1). The immunostimulatory plasmid preferably consists of a nucleic acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of pMB75.6 (SEQ ID NO: 1). In some aspects, the immunostimulatory plasmid more preferably consists of the sequence of pMB75.6 (SEQ ID NO: 1).

In some aspects, the present invention relates to an immunostimulatory plasmid consisting of a nucleic acid sequence having at least 80% sequence identity with the sequence of pGCMB75.6 (SEQ ID NO: 2). The immunostimulatory plasmid preferably consists of a nucleic acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of pGCMB75.6 (SEQ ID NO: 2). In some aspects, the immunostimulatory plasmid more preferably consists of the sequence of pGCMB75.6 (SEQ ID NO: 2).

Another important aspect of this invention provides for immunostimulatory DNA sequences or immunostimulatory plasmids capable of stimulating an immune response including nucleic acid sequences that hybridize under high stringency conditions to SEQ ID NO: 1 or SEQ ID NO: 2. Suitable nucleic acid sequences include those that are homologous, substantially similar, or identical to the nucleic acids of the present invention. In some aspects, homologous nucleic acid sequences will have a sequence similarity of at least about 75%, 76%, 77%, 78%, 79%, 80% 81%, 82%, 83%, 84%, 85%, 86%, 87%, 88%, 89%, 90%, 91%, 92%, 93%, 94%, 95%, 96%, 97%, 9%, 99%, or 100% to SEQ ID NO: 1 or the respective complementary sequence. In other aspects, homologous nucleic acid sequences will have a sequence similarity of at least about 75%, 76%, 77%, 78%, 79%, 80% 81%, 82%, 83%, 84%, 85%, 86%, 88%, 89%, 90%, 91%, 92%, 93%, 94%, 95%, 96%, 97%, 98%, 99%, or 100% to SEQ ID NO: 2 or the respective complementary sequence. Sequence similarity may be calculated using a number of algorithms known in the art, such as BLAST, described in Altschul, S. F., et al., *J. Mol. Diol.* 215:403-10, 1990. The nucleic acids may differ in sequence from the above-described nucleic acids due to the degeneracy of the genetic code. In general, a reference sequence will be 18 nucleotides, more usually 30 or more nucleotides, and may comprise the entire nucleic acid sequence of the composition for comparison purposes.

Nucleotide sequences that can hybridize to SEQ ID NO: 1 or SEQ ID NO: 2 are contemplated herein. Stringent hybridization conditions include conditions such as hybridization at 50° C. or higher and 0.1×SSC (15 mM sodium chloride/1.5 mM sodium citrate). Another example is overnight incubation at 42° C. in a solution of 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing in 0.1×SSC at about 65° C. Exemplary stringent hybridization conditions are hybridization conditions that are at least about 80%, 85%, 90%, or 95% as stringent as the above specific conditions. Other stringent hybridization conditions are known in the art and may also be employed to identify homologs of the nucleic acids of the invention (Current Protocols in Molecular Biology, Unit 6, pub. John Wiley & Sons, N.Y. 1989).

Mutant nucleotides of the DNA molecules described herein may be used, so long as mutants include nucleic acid sequences maintain the ability to increase the conception rate in cows as described herein. The DNA sequence of such a mutation will usually differ by one or more nucleotides or amino acids. The sequence changes may be substitutions, insertions, deletions, or a combination thereof. Techniques for mutagenesis of cloned genes are known in the art. Methods for site specific mutagenesis may be found in Gustin et al., Biotechniques 14:22, 1993; Barany, Gene 37:111-23, 1985; Colicelli et al., Mol. Gen. Genet, 199:537-9, 1985; and Sambrook et al., Molecular Cloning: A Laboratory Manual, CSH Press 1989, pp. 15.3-15.108 and all incorporated herein by reference. In summary, the invention relates to nucleic acid sequences capable of activating cytosolic DNA surveillance molecules in a subject and variants or mutants thereof. Also, the invention encompasses the intermediary RNAs encoded by the described nucleic acid sequences, as well as any resultant amino acid sequences encoded.

In some aspects, where the nucleotide sequence of the immunostimulatory plasmid varies from the sequences provided in SEQ ID NOs. 1 and 2, the CpG dinucleotides in the plasmid are preferably left intact. Alternatively, if the nucleotide sequence of the plasmid is altered such that a CpG dinucleotide is eliminated, the sequence of the plasmid may be altered at another location such that the total number of CpG dinucleotides in the plasmid remains the same. Further CpG dinucleotides in addition to those already present in the nucleotide sequence pGCMB75.6 may also be introduced into the plasmid. Thus, for example, the immunostimulatory plasmids described herein preferably comprise at least about 200, at least about 220, at least about 240, at least about 260, at least about 270, at least about 275, at least about 280, at least about 283, at least about 285, or at least about 288 CpG dinucleotides. For example, the immunostimulatory plasmid can comprise 283 CpG dinucleotides.

In some aspects, where the nucleotide sequence of the immunostimulatory plasmid varies from the sequences provided herein, the CpG motif types in the plasmid are varied to modulate the resultant activation of the cytosolic DNA surveillance molecules. For example, the number of immune stimulatory CpG motifs may be increased to increase the activation of specific cytosolic DNA surveillance molecules responsive to a specific threshold of immunostimulatory plasmid/DNA. By way of further example, the number of non-immune stimulatory CpG motifs may be increased to decrease the activation of specific cytosolic DNA surveillance molecules and/or increase activation of other DNA surveillance molecules.

In particular, the present invention relates to pharmaceutical formulations comprising any of the immunostimulatory plasmids or DNA sequences described herein and a pharmaceutically acceptable carrier.

B. Immunomodulator

Suitable immunomodulator compositions for use with the immunostimulatory plasmids described herein are described in U.S. Patent Application Publications Nos. 2012/0064151 A1 and 2013/0295167 A1 the contents of both of which are hereby incorporated by reference in their entirety.

The immunomodulator composition comprises a liposome delivery vehicle and at least one of the immunostimulatory plasmids, or DNA sequences, described herein.

A suitable liposome delivery vehicle comprises a lipid composition that is capable of delivering nucleic acid molecules to the tissues of the treated subject. A liposome delivery vehicle is preferably capable of remaining stable in a subject for a sufficient amount of time to deliver a nucleic acid molecule and/or a biological agent. For example, the liposome delivery vehicle is stable in the recipient subject for at least about five minutes, for at least about 1 hour, or for at least about 24 hours.

A liposome delivery vehicle of the present invention comprises a lipid composition that is capable of facilitating the delivery of a nucleic acid molecule into a cell. When the nucleic acid molecule encodes one or more proteins, the nucleic acid:liposome complex preferably has a transfection efficiency of at least about 1 picogram (pg) of protein expressed per milligram (mg) of total tissue protein per microgram (µg) of nucleic acid delivered. For example, the transfection efficiency of a nucleic acid:liposome complex can be at least about 10 pg of protein expressed per mg of total tissue protein per µg of nucleic acid delivered; or at least about 50 pg of protein expressed per mg of total tissue protein per µg of nucleic acid delivered. The transfection efficiency of the complex may be as low as 1 femtogram (fg) of protein expressed per mg of total tissue protein per µg of nucleic acid delivered, with the above amounts being more preferred.

A preferred liposome delivery vehicle of the present invention is between about 100 and 500 nanometers (nm) in diameter. For example, the liposome delivery vehicle can be between about 150 and 450 nm or between about 200 and 400 nm in diameter.

Suitable liposomes include any liposome, such as those commonly used in, for example, gene delivery methods known to those of skill in the art. Preferred liposome delivery vehicles comprise multilamellar vesicle (MIN) lipids and extruded lipids. Methods for preparation of MLVs are well known in the art. More preferred liposome delivery vehicles comprise liposomes having a polycationic lipid composition (i.e., cationic liposomes) and/or liposomes having a cholesterol backbone conjugated to polyethylene glycol. Exemplary cationic liposome compositions include, but are not limited to, N-[1-(2,3-dioleyloxy)propyl]-N,N,N-trimethylammonium chloride (DOTMA) and cholesterol, N-[1-(2,3-dioleoyloxy)propyl]-N,N,N-trimethylammonium chloride (DOTAP) and cholesterol, 1-[2-(oleoyloxy)ethyl]-

2-oleyl-3-(2-hydroxyethyl)-imidazolinium chloride (DOTIM) and cholesterol, dimethyldioctadecylammonium bromide (DDRB) and cholesterol, and combinations thereof. A most preferred liposome composition for use as a delivery vehicle includes DOTIM and cholesterol.

A suitable nucleic acid molecule includes any of the immunostimulatory plasmids described herein. Coding nucleic acid sequences encode at least a portion of a protein or peptide, while non-coding sequence does not encode any portion of a protein or peptide. According to the present invention, "non-coding" nucleic acids can include regulatory regions of a transcription unit, such as a promoter region. The term, "empty vector" can be used interchangeably with the term "non-coding," and particularly refers to a nucleic acid sequence in the absence of a protein coding portion, such as a plasmid vector without a gene insert. Expression of a protein encoded by the plasmids described herein is not required for activation of cytosolic DNA surveillance molecules; therefore the plasmids need not contain any coding sequences operatively linked to a transcription control sequence. However, further advantages may be obtained (i.e., antigen-specific and enhanced immunity) by including in the composition nucleic acid sequence (DNA or RNA) which encodes an immunogen and/or a cytokine. Such a nucleic acid sequence encoding an immunogen and/or a cytokine may be included in the immunostimulatory plasmids described herein, or can be included in a separate nucleic acid (e.g., a separate plasmid) in the composition.

Complexing a liposome with the immunostimulatory plasmids described herein may be achieved using methods standard in the art or as described in U.S. Pat. No. 6,693,086, the contents of which are hereby incorporated by reference in their entirety. A suitable concentration of a plasmid to add to a liposome includes a concentration effective for delivering a sufficient amount of the plasmid into a subject such that a systemic immune response is elicited. For example, from about 0.1 µg to about 10 µg of plasmid can be combined with about 8 nmol liposomes, from about 0.5 µg to about 5 µg of plasmid can be combined with about 8 nmol liposomes, or about 1.0 µg of plasmid can be combined with about 8 nmol liposomes. The ratio of plasmid to lipid (µg plasmid:nmol lipid) in a composition can be at least about 1:1 plasmid:lipid by weight (e.g., 1 µg plasmid:1 nmol lipid). For example, the ratio of plasmid to lipids can be at least about 1:5, at least about 1:10, or at least about 1:20. Ratios expressed herein are based on the amount of cationic lipid in the composition, and not on the total amount of lipid in the composition. The ratio of plasmid to lipids in a composition of the invention is suitably from about 1:1 to about 1:80 plasmid:lipid by weight; from about 1:2 to about 1:40 plasmid:lipid by weight; from about 1:3 to about 1:30 plasmid:lipid by weight; or from about 1:6 to about 1:15 plasmid:lipid by weight.

C. Biological Agent

Any of the immunomodulator compositions described herein can further comprise at least one biological agent, in addition to the liposome delivery vehicle and at least one of the plasmids described herein.

Suitable biological agents are agents that are effective in preventing or treating diseases. Such biological agents include immune enhancer proteins, immunogens, vaccines, antimicrobials or any combination thereof. Suitable immune enhancer proteins are those proteins known to enhance immunity. By way of a non-limiting example, a cytokine, which includes a family of proteins, is a known immunity enhancing protein family. Suitable immunogens are proteins which elicit a humoral and/or cellular immune response such that administration of the immunogen to a subject mounts an immunogen-specific immune response against the same or similar proteins that are encountered within the tissues of the subject. An immunogen may include a pathogenic antigen expressed by a bacterium, a virus, a parasite or a fungus. Preferred antigens include antigens derived from organisms which cause an infectious disease in a subject. According to the present invention, an immunogen may be any portion of a protein, naturally occurring or synthetically derived, which elicits a humoral and/or cellular immune response. As such, the size of an antigen or immunogen may be as small as about 5-12 amino acids and as large as a full length protein, including any sizes in between. The antigen may be a multimer protein or fusion protein. The antigen may be a purified antigen. Alternatively, the immune enhancer protein or immunogen can be encoded by the immunostimulatory plasmid or by another nucleic acid included in the immunomodulator composition. Where the immune enhancer protein or immunogen is encoded by a nucleic acid molecule in the immunomodulator composition, the nucleic acid sequence encoding the immune enhancer protein or immunogen is operatively linked to a transcription control sequence, such that the immunogen is expressed in a tissue of a subject, thereby eliciting an immunogen-specific immune response in the subject, in addition to the non-specific immune response. Techniques to screen for immunogenicity, such as pathogen antigen immunogenicity or cytokine activity are known to those of skill in the art and include a variety of in vitro and in vivo assays.

Where the biological agent is a vaccine, the vaccine may include a live, infectious, viral, bacterial, or parasite vaccine or a killed, inactivated, viral, bacterial, or parasite vaccine. One or more vaccines, live or killed viral vaccines, may be used in combination with the immunomodulator composition of the present invention. Suitable vaccines include those known in the art for avian or bovine species.

The biological agent can be an antimicrobial. Suitable antimicrobials include: quinolones, preferably fluoroquinolones, β-lactams, and macrolide-lincosamidestreptogramin (MLS) antibiotics.

Suitable quinolones include benofloxacin, binfloxacin, cinoxacin, ciprofloxacin, clinafloxacin, danofloxacin, difloxacin, enoxacin, enrofloxacin, fleroxacin, gemifloxacin, ibafloxacin, levofloxacin, lomefloxacin, marbofloxacin, moxifloxacin, norfloxacin, ofloxacin, orbifloxacin, pazufloxacin, pradofloxacin, perfloxacin, sarafloxacin, sparfloxacin, temafloxacin, and tosufloxacin. Preferred fluoroquinolones include ciprofloxacin, danofloxacin, enrofloxacin, moxifloxacin, and pradofloxacin. Suitable naphthyridones include nalidixic acid. Suitable β-lactams include penicillins (e.g., amoxicillin, ampicillin, azlocillin, benzathine penicillin, benzylpenicillin, carbenicillin, cloxacillin, co-amoxiclav [i.e. amoxicillin/clavulanic acid], dicloxacillin, flucloxacillin, methicillin, mezlocillin, nafcillin, oxacillin, phenoxymethylpenicillin, piperacillin, procaine penicillin, temocillin, and ticarcillin); cephalosporins (e.g., cefaclor, cefalonium, cefamandole, cefapririn, cefazolin, cefepime, cefixime, cefotaxime, cefoxitin, cefpirome, cefpodoxime, cefquinome, ceftazidime, ceftiofur, ceftriaxone, cefuroxime, cephalexin, cephalothin, and defotetan); carbapenems and penems (e.g., doripenem, ertapenem, faropenem, imipenem, and meropenem); monobactams (e.g., aztreonam, nocardicin A, tabtoxinine-β-lactam, and tigemonam); and β-lactamase inhibitors (e.g., clavulanic acid, sulbactam, and tazobactam). Preferred β-lactams include cephalosporins, in particular, cefazolin.

Suitable MLS antibiotics include clindamycin, lincomycin, pirlimycin, and any macrolide antibiotic. A preferred lincosamide antibiotic is pirlimycin.

Other antimicrobials include aminoglycosides, clopidol, dimetridazoles, erythromycin, framycetin, furazolidone, halofuginone, 2-pyridones, robenidine, sulfonamides, tetracyclines, trimethoprim, various pleuromutilins (e.g., tiamulin and valnemulin), and various streptomycin (e.g., monensin, narasin, and salinomycin).

II. Methods

A. Methods of Immune Stimulation

In one embodiment of the invention, an immune response is elicited in a female member of the bovine species by administering an effective amount of an immunomodulator composition to the female member of the bovine species. The effective amount is sufficient to elicit an immune response in the female member of the bovine species. The immunomodulator includes a liposome delivery vehicle and a nucleic acid molecule.

In one embodiment, the effective amount of the immunomodulator is from about 1 micrograms to about 1000 micrograms per animal. In another embodiment, the effective amount of the immunomodulator is from about 5 micrograms to about 500 micrograms per animal. In yet another embodiment, the effective amount of the immunomodulator is from about 10 micrograms to about 100 micrograms per animal. In a further embodiment, the effective amount of the immunomodulator is from about 10 micrograms to about 50 micro grams per animal.

In another embodiment of the invention, an immune response is elicited in a female member of the bovine species by administering an effective amount of an immunomodulator, which includes a liposome delivery vehicle, an isolated nucleic acid molecule, and a biological agent. It is contemplated that the biological agent may be mixed with or coadministered with the immunomodulator or independently thereof. Independent administration may be prior to or after administration of the immunomodulator. It is also contemplated that more than one administration of the immunomodulator or biological agent may be used to extend enhanced immunity. Furthermore, more than one biological agent may be co-administered with the immunomodulator, administered prior to the immunomodulator, administered after administration of the immunomodulator, or concurrently.

B. Conception Rates

The methods of the invention are useful for increasing conception rates in cows. In preferred embodiments, the conception rate in cows increases relative to the conception rate in a control population. In some preferred embodiments, the conception rate in cows increases relative to the conception rate in a control population as measured by a p-value of $\leq 0.05$.

The methods of the invention are useful for increasing first service conception rates in cows. As used herein, first service conception rate refers to the proportion of cows bred to artificial insemination that conceived to the first insemination. In preferred embodiments, the first service conception rate in cows increases relative to the first service conception rate in a control population. In some preferred embodiments, the first service conception rate in cows increases relative to the first service conception rate in a control population as measured by a p-value of $\leq 0.05$.

The methods of the invention are useful for increasing conception rates in non-cycling cows. As used herein, "non-cycling" refers to cows not detected in oestrus by observation or by removal of tail paint approximately 30 days prior to the planned start of breeding. In preferred embodiments, the conception rate in non-cycling cows increases relative to the conception rate in a control population. In some preferred embodiments, the conception rate in non-cycling cows increases relative to the conception rate in a control population as measured by a p-value of $\leq 0.05$.

The methods of the invention are useful for increasing first-service conception rates in non-cycling cows. In preferred embodiments, the first service conception rate in non-cycling cows increases relative to the first service conception rate in a control population. In some preferred embodiments, the first service conception rate in non-cycling cows increases relative to the first service conception rate in a control population as measured by a p-value of $\leq 0.05$.

C. Administration

A variety of administration routes are available. The particular mode selected will depend, of course, upon the particular biological agents selected, the age and general health status of the subject, the particular condition being treated and the dosage required for therapeutic efficacy. The methods of this invention may be practiced using any mode of administration that produces effective levels of an immune response without causing clinically unacceptable adverse effects. The compositions may conveniently be presented in unit dosage form and may be prepared by any of the methods well known in the art.

Vaccination of the bovine species can be performed at any age. The vaccine may be administered intravenously, intramuscularly, intradermal, intraperitoneal, subcutaneously, by spray/aerosol, orally, intraocularly, intratracheally, intranasal, or by other methods known in the art. Further, it is contemplated that the methods of the invention may be used based on routine vaccination schedules. The immunomodulator may also be administered intravenously, intramuscularly, subcutaneously, by spray, orally, intraocularly, intratracheally, nasally, or by other methods known in the art. In one embodiment, the immunomodulator is administered subcutaneously. In another embodiment, the immunomodulator is administered intramuscularly. In yet another embodiment, the immunomodulator is administered as a spray. In a further embodiment, the immunomodulator is administered orally.

In one embodiment, the immunomodulator is administered by itself to the animal prior to parturition. In another embodiment, the immunomodulator is administered by itself to the animal post parturition. In yet another embodiment, the immunomodulator is administered by itself to the animal at the same time as parturition. In still another embodiment, the immunomodulator is administered by itself to the animal both prior to parturition and at the same time as parturition. In a further embodiment, the immunomodulator composition is co-administered at the same time as the vaccination prior to parturition. In yet a further embodiment, the immunomodulator composition is co-administered at the same time as the vaccination at the same time as parturition. The co-administration may include administering the vaccine and immunomodulator in the same general location on the animal at two different sites next to each other (i.e., injections next to each other at the neck of the animal), on opposing sides of the animal at the same general location (i.e., one on each side of the neck), or on different locations of the same animal. In another embodiment, the immunomodulator composition is administered prior to vaccination and parturition. In a further embodiment, the immunomodulator composition is administered after vaccination but prior to parturition. In a further embodiment, the immunomodulator composition is administered after parturition to an animal that has been vaccinated prior to parturition. A skilled artisan will recognize that administration routes may vary depending upon the subject and the health or state of the subject.

In one embodiment, the immunomodulator is administered by itself to the animal prior to breeding. In another embodiment, the immunomodulator is administered by itself to the animal post breeding. In yet another embodiment, the immunomodulator is administered by itself to the animal at the same time as breeding. In still another embodiment, the immunomodulator is administered by itself to the animal both prior to breeding and at the same time as breeding. In a further embodiment, the immunomodulator composition is co-administered at the same time as the vaccination prior to breeding. In yet a further embodiment, the immunomodulator composition is co-administered at the same time as the vaccination at the same time as breeding. The co-administration may include administering the vaccine and immunomodulator in the same general location on the animal at two different sites next to each other (i.e., injections next to each other at the neck of the animal), on opposing sides of the animal at the same general location (i.e., one on each side of the neck), or on different locations of the same animal. In another embodiment, the immunomodulator composition is administered prior to vaccination and breeding. In a further embodiment, the immunomodulator composition is administered after vaccination but prior to breeding. In a further embodiment, the immunomodulator composition is administered after breeding to an animal that has been vaccinated prior to breeding. A skilled artisan will recognize that administration routes may vary depending upon the subject and the health or state of the subject.

In one embodiment, the immunomodulator is administered from about 1 to about 14 days prior to challenge or from about 1 to about 14 days post challenge. In another embodiment, the immunomodulator is administered from about 1 to about 7 days prior to challenge or from about 1 to about 7 days post challenge. In yet another embodiment, the immunomodulator is administered 1, 2, 3, 4, 5, 6, 7 days prior to challenge or 1, 2, 3, 4, 5, 6, 7 days post challenge. In a preferred embodiment, the immunomodulator is administered 3 days prior to challenge or 3 days post challenge.

Other delivery systems may include time-release, delayed release or sustained release delivery systems. Such systems can avoid repeated administrations of the compositions therefore increasing convenience. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109.

Delivery systems also include non-polymer systems that are lipids including sterols such as cholesterol, cholesterol esters and fatty acids or neutral fats such as mono-di and tri-glycerides; hydrogel release systems; sylastic systems; peptide based systems; wax coatings; compressed tablets using convention binders and excipients; partially fused implants; and the like. Specific examples include, but are not limited to erosional systems in which an agent of the invention is contained in a form within a matrix such as those described in U.S. Pat. Nos. 4,452,775, 4,675,189 and 5,736,152, and diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

As various changes could be made in the above composition, products and methods without departing from the scope of the invention, it is intended that all matter contained in the above description and in the examples given below, shall be interpreted as illustrative and not in a limiting sense.

Definitions

The term "effective amount" refers to the amount necessary or sufficient to realize a desired biologic effect. For example, an effective amount of immunomodulator for treating or preventing an infectious disease is that amount necessary to cause the development of an immune response upon exposure to the microbe, thus causing a reduction in the amount of microbe within the subject and preferably to the eradication of the microbe. The effective amount for any particular application can vary depending on such factors as the disease or condition being treated, the size of the subject, or the severity of the disease or condition. One of ordinary skill in the art can empirically determine the effective amount of immunomodulator without necessitating undue experimentation.

The term "cow" as used herein refers to any member of the bovine species that is capable of bearing offspring, including without limitation, female bovine, cows, and heifers.

The term "cytokine" refers to an immune enhancing protein family. The cytokine family includes hematopoietic growth factor, interleukins, interferons, immunoglobulin superfamily molecules, tumor necrosis factor family molecules and chemokines (i.e. proteins that regulate the migration and activation of cells, particularly phagocytic cells). Exemplary cytokines include, without limitation, interleukin-2 (IL-2), interleukin-12 (IL12), interleukin-15 (IL-15), interleukin-18 (IL-18), interferon-α (IFNα), and interferon-γ (IFNγ).

The term "elicit" can be used interchangeably with the terms activate, stimulate, generate or upregulate.

The term "eliciting an immune response" in a subject refers to specifically controlling or influencing the activity of the immune response, and can include activating an immune response, upregulating an immune response, enhancing an immune response and/or altering an immune response (such as by eliciting a type of immune response which in turn changes the prevalent type of immune response in a subject from one which is harmful or ineffective to one which is beneficial or protective).

The term "operatively linked" refers to linking a nucleic acid molecule to a transcription control sequence in a manner such that the molecule is able to be expressed when transfected (i.e., transformed, transduced or transfected) into a host cell. Transcriptional control sequences are sequences which control the initiation, elongation, and termination of transcription. Particularly important transcription control sequences are those which control transcription initiation, such as promoter, enhancer, operator and repressor sequences. A variety of such transcription control sequences are known to those skilled in the art. Preferred transcription control sequences include those which function in avian, fish, mammalian, bacteria, plant, and insect cells. While any transcriptional control sequences may be used with the invention, the sequences may include naturally occurring transcription control sequences naturally associated with a sequence encoding an immunogen or immune stimulating protein.

The terms "nucleic acid molecule" and "nucleic acid sequence" can be used interchangeably and include DNA. RNA, or derivatives of either DNA or RNA. The terms also include oligonucleotides and larger sequences, including both nucleic acid molecules that encode a protein or a fragment thereof, and nucleic acid molecules that comprise regulatory regions, introns, or other non-coding DNA or RNA. Typically, an oligonucleotide has a nucleic acid sequence from about 1 to about 500 nucleotides, and more typically, is at least about 5 nucleotides in length. The nucleic acid molecule can be derived from any source, including mammalian, fish, bacterial, insect, viral, plant, or synthetic sources. A nucleic acid molecule can be produced by methods commonly known in the art such as recombinant DNA technology (e.g., polymerase chain reaction (PCR), amplification, cloning) or chemical synthesis. Nucleic acid molecules include natural nucleic acid molecules and homologues thereof, including, but not limited to, natural allelic variants and modified nucleic acid molecules in which nucleotides have been inserted, deleted, substituted, or inverted in such a manner that such modifications do not substantially interfere with the nucleic acid molecule's ability to encode an immunogen or immune stimulating protein useful in the methods of the present invention. A nucleic acid homologue may be produced using a number of methods known to those skilled in the art (see, for example. Sambrook et al., Molecular Cloning: A Laboratory Manual, Cold Spring Harbor Labs Press, 1989), which is incorporated herein by reference. Techniques to screen for immunogenicity, such as pathogen antigen immunogenicity or cytokine activity are known to those of skill in the art and include a variety of in vitro and in vivo assays.

The terms "selectable marker" and "selectable marker gene" refer to a gene that encodes a product that protects the organism in which the gene is expressed from a selective agent (e.g., an antibiotic) or a condition that would normally kill the organism or inhibit its growth. Selectable marker genes are most commonly antibiotic resistance genes (e.g., kanamycin resistance genes, ampicillin resistance genes, chloramphenicol resistance genes, tetracycline resistance genes, etc.). Thus, for example, when *E. coli* cells are subjected to a transformation procedure to introduce a plasmid encoding a kanamycin resistance gene and then grown on or in media containing kanamycin, only the *E. coli* cells that have successfully taken up the plasmid and expressed the kanamycin resistance gene will survive. The terms "selectable marker" and "selectable marker gene" also include genes that code for enzymes involved in the synthesis of a compound that is essential for the growth of an organism. When introduced into an auxotrophic organism that is unable to synthesize the essential compound, such genes allow the organism to grow in a medium that has been supplemented with the essential compound. For example, bacterial cells that are auxotrophic for the amino acid lysine due to a mutation in or the absence of an enzyme involved in lysine biosynthesis normally are unable to grown on media that has not been supplemented with lysine. When such bacteria are subjected to a transformation procedure to introduce a plasmid encoding the enzyme involved in lysine biosynthesis, the bacteria that have successfully taken up the plasmid and expressed the enzyme will survive when grown on media that has not been supplemented with lysine. The terms "selectable marker" and "selectable marker gene" further include genes that allow for poison/antidote selection. For example, the ccdB gene encodes a protein that binds to DNA gyrase, an essential enzyme for cell division. Upon binding to DNA gyrase, the ccdB gene product impairs gene replication and induces cell death. Thus, bacterial expressing the ccdB gene product cannot survive. The ccdA gene encodes a protein (the "antidote") that acts as a natural inhibitor of the ccdB gene product. Thus, when bacteria having the ccdB gene in their bacterial genome are subjected to a transformation procedure to introduce a plasmid encoding the ccdA gene product, only the cells that successfully take up the plasmid and express the ccdA gene will survive.

The to terms "screenable marker" and "screenable marker gene" refer to a gene that encodes a product that allows an observer to distinguish between cells expressing the screenable marker gene and cells that are not expressing the screenable marker gene. Screenable marker gene systems are well known in the art and include, for example, lacZ genes and genes encoding fluorescent proteins such as green fluorescent protein (GFP), yellow fluorescent protein (YFP), red fluorescent protein (RFP), blue fluorescent protein (BFP), or cyan fluorescent protein (CFP).

TABLE 1

Plasmid DNA sequences

| Plasmid | SEQ ID NO. | SEQUENCE |
|---------|------------|----------|
| pMB75.6 | 1 | ctaaattgtaagcgttaatattttgttaaaattcgcgttaaattttttgttaaatcagctcatttttaaccaata |
|         |   | ggccgaaatcggcaaaatcccttataaatcaaaagaatagaccgagatagggttgagtgttgttcca |
|         |   | gtttggaacaagagtccactattaaagaacgtggactccaacgtcaaagggcgaaaaaccgtctatc |
|         |   | agggcgatggcccactacgtgaaccatcaccctaatcaagttttttggggtcgaggtgccgtaaagc |
|         |   | actaaatcggaaccctaaagggagcccccgatttagagcttgacggggaaagccggcgaacgtg |
|         |   | gcgagaaaggaagggaagaaagcgaaaggagcgggcgctagggcgctggcaagtgtagcggt |
|         |   | cacgctgcgcgtaaccaccacacccgccgcttaatgcgccgctacagggcgcgtcccattcgc |
|         |   | cattcaggctgcgcaactgtttgggaagggcgatcggtgcgggcctcttcgctattacgccagctgg |
|         |   | cgaaagggggatgtgctgcaaggcgattaagttgggtaacgccagggttttcccagtcacgacgtt |
|         |   | gtaaaacgacggccagtgagcgcgcgtaatacgactcactatagggcgaattgggtaccgggccc |
|         |   | cccctcgagcaggatctatacattgaatcaatattggcaattagccatattagtcattggttatatagcat |
|         |   | aaatcaatattggctattggccattgcatacgttgtatctatatcataatatgtacatttatattggctcatg |
|         |   | tccaatatgaccgccatgttgacattgattattgactagttattaatagtaatcaattacggggtcattagt |
|         |   | tcatagcccatatatggagttccgcgttacataacttacggtaaatggcccgcctggctgaccgccca |
|         |   | acgaccccccgcccattgacgtcaataatgacgtatgttcccatagtaacgccaatagggactttccat |
|         |   | tgacgtcaatgggtggagtatttacggtaaactgcccacttggcagtacatcaagtgtatcatatgcca |
|         |   | agtccgccccctattgacgtcaatgacggtaaatggcccgcctggcattatgcccagtacatgaccctt |

TABLE 1-continued

Plasmid DNA sequences

| Plasmid | SEQ ID NO. | SEQUENCE |
|---|---|---|
| | | acgggactttcctacttggcagtacatctacgtattagtcatcgctattaccatggtgatgcggttttgg<br>cagtacatcaatgggcgtggatagcggtttgactcacggggatttccaagtctccaccccattgacgt<br>caatgggagtttgttttggcaccaaaatcaacgggactttccaaaatgtcgtaacaactccgccccatt<br>gacgcaaatgggcggtaggcgtgtacggtgggaggtctatataagcagagctcgtttagtgaaccg<br>tcagatcgcctggagacgccatccacgctgttttgacctccataagagacacgggaccgatccag<br>cctcccctcgaagccgatctgataacggtaccgataagctggcggccgattaagctacagaagttg<br>gtcgtgaggcactgggcaggtaagtatcaaggttacaagacaggtttaaggagaccaatagaaact<br>gggcttgtcgagacagagaagactcttgcgtttctgataggcacctattggtcttactgacatccacttt<br>gcctttctctccacaggtgtccactcccaggttcaattacagctcttaagcagccgaagcttgatatc<br>gaattcctgcagcccggggatccactagttctagagcggccgccaccgcggtggagctcgaatt<br>atcagatcgattaataactatgctcaaaaattgtgtaccttttagcttttttaatttgtaaagggggtaataag<br>gaatatttgatgtatagtgccttgactagagatcataatcagccataccacatttgtagaggttttacttg<br>ctttaaaaaacctcccacacctcccctgaacctgaaacataaaatgaatgcaattgttgttgttaactt<br>gtttattgcagcttataatggttacaaataaagcaatagcatcacaaatttcacaaataaagcattttttc<br>actgcattctagttgtggtttgtccaaactcatcaatgtatcttatcatgtctggatcatcagatctgccgg<br>tctccctatagtgagtcgtattaatttcgataagccaggttaacctgcattaatgaatcggccaacgcg<br>cggggagaggcggtttgcgtattgggcgctcttccgcttcctcgctcactgactcgctgcgctcggt<br>cgttcggctgcggcgagcggtatcagctcactcaaaggcggtaatacggttatccacagaatcagg<br>ggataacgcaggaaagaacatgtgagcaaaaggccagcaaaaggccaggaaccgtaaaaaggc<br>cgcgttgctggcgtttttccataggctccgcccccctgacgagcatcacaaaaatcgacgctcaagt<br>cagaggtggcgaaacccgacaggactataaagataccaggcgtttccccctggaagctccctcgt<br>gcgctctcctgttccgaccctgccgcttaccggatacctgtccgcctttctcccttcgggaagcgtgg<br>cgctttctcatagctcacgctgtaggtatctcagttcggtgtaggtcgttcgctccaagctgggctgtgt<br>gcacgaaccccccgttcagcccgaccgctgcgccttatccggtaactatcgtcttgagtccaaccg<br>gtaagacacgacttatcgccactggcagcagccactggtaacaggattagcagagcgaggtatgta<br>ggcggtgctacagagttcttgaagtggtggcctaactacggctacactagaagaacagtatttggtat<br>ctgcgctctgctgaagccagttaccttcggaaaaagagttggtagctcttgatccggcaaacaaacc<br>accgctggtagcggtggtttttttgttgcaagcagcagattacgcgcagaaaaaaaggatctcaaga<br>agatcctttgatcttttctacggggtctgacgctcagtggaacgaaaactcacgttaagggattttggtc<br>atgagcgcgcctaggcttttgcaaagatcgatcaagagacaggatgaggatcgtttcgcatgattga<br>acaagatggattgcacgcaggttctccggccgcttgggtggagaggctattcggctatgactgggc<br>acaacagacaatcggctgctctgatgccgccgtgttccggctgtcagcgcaggggcgcccggttct<br>ttttgtcaagaccgacctgtccggtgccctgaatgaactgcaagacgaggcagcgcggctatcgtg<br>gctggccacgacgggcgttccttgcgcagctgtgctcgacgttgtcactgaagcgggaagggact<br>ggctgctattgggcgaagtgccggggcaggatctcctgtcatctcaccttgctcctgccgagaaagt<br>atccatcatggctgatgcaatgcggcggctgcatacgcttgatccggctacctgcccattcgaccac<br>caagcgaaacatcgcatcgagcgagcacgtactcggatggaagccggtcttgtcgatcaggatgat<br>ctggacgaagagcatcaggggctcgcgccagccgaactgttcgccaggctcaaggcgagcatgc<br>ccgacggcgaggatctcgtcgtgacccatggcgatgcctgcttgccgaatatcatggtggaaaatg<br>gccgcttttctggattcatcgactgtggccggctgggtgtggcggaccgctatcaggacatagcgtt<br>ggctacccgtgatattgctgaagagcttggcggcgaatgggctgaccgcttcctcgtgctttacggta<br>tcgccgctcccgattcgcagcgcatcgccttctatcgccttcttgacgagttcttctgagcgggactct<br>ggggttcgaaatgaccgaccaagcgacgcccaacctgccatcacgagatttcgattccaccgccg<br>ccttctatgaaaggttgggcttcggaatcgttttccgggacgccggctggatgatcctccagcgcgg<br>ggatctcatgctggagttcttcgcccaccctaggcgcgctcatgagcggatacatatttgaatgtattt<br>agaaaaataaacaaataggggttccgcgcacatttccccgaaaagtgccac |
| pGCMB75.6 | 2 | tgaccgcccaacgaccccgcccattgacgtcaataatgacgtatgttcccatagtaacgccaatag<br>ggactttccattgacgtcaatgggtggagtatttacggtaaaactgcccacttggcagtacatcaagtgt<br>atcatatgccaagtccgccccctattgacgtcaatgacggtaaatggcccgcctggcattatgccca<br>gtacatgaccttacgggactttcctacttggcagtacatctacgtattagtcatcgctattaccatggtg<br>atgcggttaggcagtacatcaatgggcgtggatagcggtttgactcacggggatttccaagtacca<br>ccccattgacgtcaatgggagtttgttttggcaccaaaatcaacgggactttccaaaatgtcgtaacaa<br>ctccgccccattgacgcaaatgggcggtaggcgtgtacggtgggaggtctatataagcagagctcg<br>tttagtgaaccgtcagatcgcaggagacgccatccacgagttagacctccatagaagacaccgg<br>gaccgatccagcctcccctcgaagccgatctgataacggtaccgataagctggcggccgattaagc<br>tacagaagttggtcgtgaggcactgggcaggtaagtatcaaggttacaagacaggtttaaggagac<br>caatagaaactgggcttgtcgagacagagaagactatgcgtttctgataggcacctattggtatact<br>gacatccactttgcctttctctccacaggtgtccactcccaggttcaattacagctcttaagcagccgc<br>aagcttgatatcgaattcctgcagcccggggatccactagttctagagcggccgccaccgcggtg<br>gagctcgaattatcagatcgattaataactatgctcaaaaattgtgtaccttttagcttttttaatttgtaaag<br>gggttaataaggaatatttgatgtatagtgccttgactagagatcataatcagccataccacatttgtag<br>aggttttacttgctttaaaaaacctcccacacctcccctgaacctgaaacataaaatgaatgcaattgt<br>tgttgttaacttgtttattgcagcttataatggttacaaataaagcaatagcatcacaaatttcacaaataa<br>agcattttttttcactgcattctagttgtggtttgtccaaactcatcaatgtatcttatcatgtctggatcatca<br>gatctgccggtaccctatagtgagtcgtattaatttcgataagccaggttaacctgcattaatgaatcg<br>gccaacgcgcggggagaggcggtttgcgtattgggcgctcttccgcttcctcgctcactgactcgct<br>gcgctcggtcgttcggctgcggcgagcggtatcagctcactcaaaggcggtaatacggttatccac<br>agaatcaggggataacgcaggaaagaacatgtgagcaaaaggccagcaaaaggccaggaaccg<br>taaaaaggccgcgttgctggcgtttttccataggctccgcccccctgacgagcatcacaaaaatcga<br>cgctcaagtcagaggtggcgaaacccgacaggactataaagataccaggcgtttcccccctggaag<br>ctccctcgtgcgctctcctgttccgaccctgccgcttaccggatacctgtccgcctttctcccttcggg<br>aagcgtggcgctttctcatagctcacgctgtaggtatctcagttcggtgtaggtcgttcgctccaagct<br>gggctgtgtgcacgaaccccccgttcagcccgaccgctgcgccttatccggtaactatcgtcttgag |

TABLE 1-continued

Plasmid DNA sequences

| Plasmid | SEQ ID NO. | SEQUENCE |
|---|---|---|
| | | tccaacccggtaagacacgacttatcgccactggcagcagccactggtaacaggattagcagagc<br>gaggtatgtaggcggtgctacagagttcttgaagtggtggcctaactacggctacactagaagaaca<br>gtatttggtatagcgctctgagaagccagttaccttcggaaaaagagttggtagctcttgatccggc<br>aaacaaaccaccgctggtagcggtggtttttttgtttgcaagcagcagattacgcgcagaaaaaaag<br>gatctcaagaagatcctttgatcttttctacggggtctgacgctcagtggaacgaaaactcacgttaag<br>ggattttggtcatgggcgcgcctaggcttttgcaaagatcgatcaagagacaggatgaggatcgtttc<br>gcagcttttcattctgactgcaacgggcaataagtctctgtgtggattaaaaaaagagtgtctgatagc<br>agatctgaactggttacctgccgtgagtaaattaaaattttattgacttaggtcactaaggcgccttgc<br>gctgaggttgcgtcgtgatatcatcagggcagaccggttacatcccctaacaagctgtataaagag<br>aaatactatctcattggcgttgcccgcacctgacagtgcgacgttgggctgcgtccgtcgaccaacg<br>gtaccgaggtaacagcccaatctatccatgatctcggccaggccgggtcggccgttatgcagcccg<br>gctcgggtatgaagccattaaggagccgaccagcgcgaccgggcggccggtcacgtgcctct<br>gctgaagcctgcctgtcactccctgcgcggcgtacccgccgttctcatcgagtaggaccggatcg<br>cgaccccggacgggccctgggcccaggagcggcctatgacaaatgccgggtagcgatccggca<br>ttcagcattgactgcgcacggatccagtccttgcaggagccttatgccgaccgtagcaaaaaatgag<br>cccgagccgatcgcgagttgtgatccggtcccgccgattgccggtcgcgatgacggtcctgtgtaa<br>gcgttatcgttaccaattgtttaagaagtatatacgctacgaggtacttgataacttctgcgtagcatac<br>atgaggttttgtataaaaatggcgggcgatatcaacgcagtgtcagaaatccgaaacagtctgcggg<br>actaggggttcgaaatgaccgaccaagcgacgcccaacctgccatcacgagatttcgattccacc<br>gccgccttctatgaaaggttgggcttcggaatcgttttccgggacgccggctggatgatcctccagc<br>gcggggatctcatgctggagttcttcgcccacccctaggcgcgctcatgagcggatacatatttgaat<br>gtatttagaaaaataaacaaatagggggttccgcgcacatttccccgaaaagtgccacctaaattgtaa<br>gcgttaatattttgttaaaattcgcgttaaattttttgttaaatcagctcattttttaaccaataggccgaaatc<br>ggcaaaatcccttataaatcaaaagaatagaccgagatagggttgagtgttgttccagtttggaacaa<br>gagtccactattaaagaacgtggactccaacgtcaaagggcgaaaaccgtctatcagggcgatg<br>gcccactacgtgaaccatcaccctaatcaagtttttgggtcgaggtgccgtaaagcactaaatcgg<br>aaccctaaagggagccccgatttagagatgacggggaaagccggcgaacgtggcgagaaag<br>gaagggaagaaagcgaaaggagcgggcgctaggcgctggcaagtgtagcggtcacgctgcg<br>cgtaaccaccacacccgccgcgcttaatgcgccgctacagggcgcgtcccattcgccattcaggct<br>gcgcaactgttgggaagggcgatcggtgcgggcctcttcgctattacgccagaggcgaaagggg<br>gatgtgctgcaaggcgattaagttgggtaacgccagggttttcccagtcacgacgttgtaaaacgac<br>ggccagtgagcgcgcgtaatacgactcactatagggcgaattgggtaccgggccccccctcgagc<br>aggatctatacattgaatcaatattggcaattagccatattagtcattggttatatagcataaatcaatatt<br>ggctattggccattgcatacgttgtatctatatcataatatgtacatttatattggctcatgtccaatatgac<br>cgccatgttgacattgattattgactagttattaatagtaatcaattacggggtcattagttcatagcccat<br>atatggagttccgcgttacataacttacggtaaatggcccgcctggc |
| pLacZMB75.6 | 3 | tgaccgcccaacgaccccgcccattgacgtcaataatgacgtatgttcccatagtaacgccaatag<br>ggactttccattgacgtcaatgggtggagtatttacggtaaactgcccacttggcagtacatcaagtgt<br>atcatatgccaagtccgccccctattgacgtcaatgacggtaaatggcccgcctggcattatgccca<br>gtacatgaccttacgggactttcctacttggcagtacatctacgtattagtcatcgctattaccatggtg<br>atgcggttttggcagtacatcaatgggcgtggatagcggtttgactcacggggatttccaagtctcca<br>ccccattgacgtcaatgggagtttgttttggcaccaaaatcaacgggactttccaaaatgtcgtaacaa<br>ctccgccccattgacgcaaatgggcggtaggcgtgtacggtgggaggtctatataagcagagctcg<br>tttagtgaaccgtcagatcgcctggagacgccatccacgctgttttgacctccatagaagacaccgg<br>gaccgatccagcaccccctcgaagccgatctgataacggtaccgataagaggcggccgattaagc<br>tacagaaagttggtcgtgaggcactgggcaggtaagtatcaaggttacaagacaggtttaaggagac<br>caatagaaactgggcttgtcgagacagagaagactcttgcgtttctgataggcacctattggtatact<br>gacatccacttgttgcctttctctccacaggtgtccactcccaggttcaattacagctcttaagcagccgc<br>caaaacaaaattcctcaaaaatcatcatcgaatgaatggtgaaataatttccctgaataactgtagtgtt<br>ttcagggcgcggcataataattaactatgctcaaaaattgtgtaccttttagcttttttaatttgtaaagggg<br>ttaataaggaatatttgatgtatagtgccttgactagagatcataatcagccataccacatttgtagagg<br>ttttacttgctttaaaaaacctccacaccctccccctgaacctgaaacataaaatgaatgcaattgttgtt<br>gttaaccttgtttattgcagcttataatggttacaaataaagcaatagcatcacaaatttcacaaataaagc<br>attttttttcactgcattctagttgtggtttgtccaaactcatcaatgtatcttatcatgtctggatcatcagat<br>ctgccggtctccctatagtgagtcgtattaatttcgataagccaggttaacctgcattaatgaatcggcc<br>aacgcgcggggagaggcggtttgcgtattgggcgctatcgcttcctcgctcactgactcgagcg<br>ctcggtcgttcggctgcggcgagcggtatcagctcactcaaaggcggtaatacggttatccacaga<br>atcagggggataacgcaggaaagaacatgtgagcaaaaggccagcaaaaggccaggaaccgtaa<br>aaaggccgcgttgctggcgtttttccataggaccgccccctgacgagcatcacaaaaatcgacg<br>ctcaagtcagaggtggcgaaacccgacaggactataaagataccaggcgtttccccctggaagctc<br>cctcgtgcgctctcctgttccgaccctgccgcttaccggatacctgtccgcctttctcccttcgggaag<br>cgtggcgctttctcatagctcacgctgtaggtatctcagttcggtgtaggtcgttcgctccaagctggg<br>ctgtgtgcacgaacccccgttcagcccgaccgctgcgccttatccggtaactatcgtcttgagtcca<br>acccggtaagacacgacttatcgccactggcagcagccactggtaacaggattagcagagcgag<br>tatgtaggcggtgctacagagttcttgaagtggtggcctaactacggctacactagaagaacagtatt<br>tggtatagcgactgagaagccagttaccttcggaaaagagttggtagctcttgatccggcaaac<br>aaaccaccgctggtagcggtggattttgtttgcaagcagcagattacgcgcagaaaaaaggatct<br>caagaagatcctttgatatttctacggggtctgacgctcagtggaacgaaaactcacgttaagggat<br>tttggtcatgggcgcgcctaggatttgcaaagatcgatcaagagacaggatgaggatcgtttcgcag<br>cttttcattctgactgcaacgggcaataagtctctgtgtggattaaaaaaagagtgtctgatagcagctt<br>ctgaactggttacctgccgtgagtaaattaaaattttattgacttaggtcactaaggcgccttgcgctga<br>ggttgcgtcgtgatatcatcagggcagaccggttacatcccctaacaagctgtataaagagaaata<br>ctatctcattggcgttgcccgcacctgacagtgcgacgttgggctgcgtccgtcgaccaacggtacc |

TABLE 1-continued

Plasmid DNA sequences

| Plasmid | SEQ ID NO. | SEQUENCE |
|---|---|---|
| | | gaggtaacagcccaatctatccatgatctcggccaggccgggtcggccgttatgcagcccggctcg |
| | | ggtatgaagccattaaggagccgacccagcgcgacccgggcggccggtcacgagcctctgctga |
| | | agcctgcctgtcactccctgcgcggcgtacccgccgttctcatcgagtaggctccggatcgcgacc |
| | | ccggacgggccctgggcccaggagcggcctatgacaaatgccgggtagcgatccggcattcagc |
| | | attgactgcgcacggatccagtccttgcaggagccttatgccgaccgtagcaaaaaatgagcccga |
| | | gccgatcgcgagttgtgatccggtcccgccgattgccggtcgcgatgacggtcctgtgtaagcgtta |
| | | tcgttaccaattgataagaagtatatacgctacgaggtacttgataacttctgcgtagcatacatgagg |
| | | ttttgtataaaaatggcggcgatatcaacgcagtgtcagaaatccgaaacagtctgcgggactctg |
| | | gggttcgaaatgaccgaccaagcgacgcccaacctgccatcacgagatttcgattccaccgccgc |
| | | cttctatgaaaggttgggcttcggaatcgttttccgggacgccggctggatgatcctccagcgcggg |
| | | gatctcatgctggagttcttcgcccacccctaggcgcgctcatgagcggatacatatttgaatgtattta |
| | | gaaaaataaacaaataggggttccgcgcacatttccccgaaaagtgccacctaaattgtaagcgtta |
| | | atattttgttaaaattcgcgttaaattttgttaaatcagctcatttttttaaccaataggccgaaatcggcaa |
| | | aatcccttataaatcaaaagaatagaccgagatagggttgagtgttgttccagtttggaacaagagtc |
| | | cactattaaagaacgtggactccaacgtcaaagggcgaaaaccgtctatcagggcgatggccca |
| | | ctacgtgaaccatcaccctaatcaagttttttgggtcgaggtgccgtaaagcactaaatcggaaccc |
| | | taaagggagcccccgatttagagcttgacggggaaagccggcgaacgtggcgagaaaggaagg |
| | | gaagaaagcgaaaggagcgggcgctagggcgctggcaagtgtagcggtcacgctgcgcgtaac |
| | | caccacacccgccgcgcttaatgcgccgctacagggcgcgtcccattcgccattcaggagcgca |
| | | actgttgggaagggcgatcggtgcgggcctatcgctattacgccagaggcgaaaggggggatgt |
| | | gctgcaaggcgattaagagggtaacgccagggttttcccagtcacgacgttgtaaaacgacggcc |
| | | agtgagcgcgcgtaatacgactcactatagggcgaattgggtaccgggccccccacgaggtcga |
| | | cggtatcgataagatgatatcgaattcctgcagcccgggggatccactagttctagagcggccgcc |
| | | accgcggtggagctccagcttagttccctttagtgagggttaattgcgcgcttggcgtaatcatggtc |
| | | atagctgttttcctgtgtgaaangttatccgctcacaattccacacaacatacgagccggaagcataaa |
| | | gtgtaaagcctggggtgcctaatgagtgagctaactcacattaattgcgttgcgc |

EXAMPLES

The following example illustrates various embodiments of the invention.

Example 1: Efficacy of Immunomodulator Composition in Increasing Conception Rates in Non-Cycling Cows The Purpose of this Study was to Assess the Effect of Modulating Immune Function at calving on reproductive outcomes of the treated cows.

Immunomodulator

The immunomodulatory used in this study was the composition described above in Example 1.

Study Animals

875 Friesian, Jersey or cross-bred cows aged ≥2 years were obtained from two commercial dairy herds Farm A and B in the Waikato district of New Zealand. The cows were selected based on being newly calved and lactating. Cows were excluded if they were treated with antibiotics, non-steroidal anti-inflammatories or corticosteroids in the 30 days preceding calving or if they exhibited gross evidence of any disease at calving. The remaining animals were blocked by age (heifers versus cows) and assigned within sequential pairs of animals presented from pre-prepared randomization lists to the treatment or placebo groups.

Treatment

Treatment was randomized and the treatment allocation was not included on any of the post treatment sampling sheets and the milk samples were assigned a unique number at accession which was used during subsequent laboratory analysis. On the day of calving (day 0) and following physical examination and enrollment, the appropriate treatment was administered by intramuscular injection into the right gluteal muscle. The injection site was swabbed with a cotton ball moistened in 70% methylated spirits prior to injection. Treatment was repeated in the evening of day 3 or the morning of day 4 and again at day 7 postpartum with injection in the right gluteal muscles.

Breeding Management

Tail paint (a heat detection aid) was applied approximately 30 days before the planned start of the breeding program. Those cows not detected in oestrus by observation or removal of the tail paint were treated with a combination of progesterone, GnRH, and prostaglandin $F_{2\alpha}$ and bred to set time artificial insemination. For the first 37 days at the Farm A site and 47 days at the Farm B site, those cows detected in standing oestrus were bred by artificial insemination. Thereafter intact bulls were run with the herd. The total length of the mating period was 77 and 80 days for Farm A and B, respectively. Cows were examined by transrectal ultrasonography at 83 and 113 days after the start of the breeding program (Farm A) and 90 and 120 days after this start of the breeding program (Farm B). Those cows detected pregnant, had the stage of gestation estimated. Where the estimated stage of gestation was within 7 days of recorded breeding, either artificial insemination or natural mating, the recorded date was accepted as the day of conception.

Results

The three-week submission rate (the proportion of cows detected and inseminated within three weeks at the start of the breeding program), the first service conception rate (the proportion of cows bred to artificial insemination that conceived to the first insemination) and the 3 and 6 week in calf rate (the proportion of cows confirmed pregnant within the first three and six weeks of the breeding program), and the final pregnancy rates were calculated.

The binomial reproductive outcomes were initially analyzed in bivariate (chi squared) analysis. Multivariate logistic regression models were then undertaken including the explanatory variables of treatment, herd, age (2, 3 and >3 years old), days in milk at the start of the breeding program (categorized as 50 to 71 days and ≥72 days) and breed (Friesian versus other breeds). Additionally, the planned start of mating to conception interval was calculated for each cow and Kaplan-Meier survival analysis was used to calculate the median days to conception.

The treatment groups were balanced for breed code and age and p-values were calculated using a chi-squared test, as depicted in Table 1.

TABLE 1

Number of cows in treated and control groups by breed code and age

|  | Treated | Control | P-value |
|---|---|---|---|
| Age Group |  |  |  |
| 2 years | 79 | 73 | 0.62 |
| 3 years | 91 | 82 | 0.48 |
| ≥4 years | 267 | 279 | 0.33 |
| Total | 437 | 434 | — |
| Breed |  |  |  |
| Fresian | 245 | 258 | 0.29 |
| Jersey | 6 | 6 | 1.00* |
| Crossbred | 186 | 169 | 0.29 |
| Total | 437 | 433 | — |

*P-value calculated using Fisher's exact test.

Additionally, the mean and median time from calving to planned start of mating was the same between the treatment and control groups, as depicted in Table 2. The P-value comparing median days from calving to planned start of breeding for the treatment and control groups was calculated using a Mann-Whitney test.

TABLE 2

Mean, standard error (SE), and median days from calving to start of breeding program for cows in the treated and control groups

|  | n | Mean | SE | Median | P-value |
|---|---|---|---|---|---|
| Treated | 437 | 72.4 | 0.43 | 75 | 0.92 |
| Control | 434 | 72.4 | 0.43 | 75 |  |

As shown in Table 3, there were no differences between treatment and control groups for the probability of submission to artificial insemination in 21 days after planned start of mating (PSM) (submission in 3 weeks), probability of conception to the first insemination after PSM (conception to first service), probability of pregnancy by 21 and 42 days (pregnant in 3 weeks and pregnant in 6 weeks, respectively) after PSM and overall pregnancy at the bivariate level. P-values were calculated using a Chi-square test.

TABLE 3

Number (%) of cows by treatment groups

|  | Treated (%) | Control (%) | P-value |
|---|---|---|---|
| Treated as a non-cycler | 75/437 (17.2) | 91/434 (21.0) | 0.15 |
| Submission in 3 weeks | 383/432 (88.7) | 394/430 (91.6) | 0.14 |
| Conception to $1^{st}$ service | 263/383 (68.7) | 254/394 (64.5) | 0.21 |
| Pregnant in 3 weeks | 273/432 (63.2) | 260/430 (60.5) | 0.41 |
| Pregnant in 6 weeks | 344/432 (79.6) | 327/430 (76.0) | 0.21 |
| Overall pregnant | 384/432 (88.9) | 383/430 (89.1) | 0.93 |

Figure 4A:
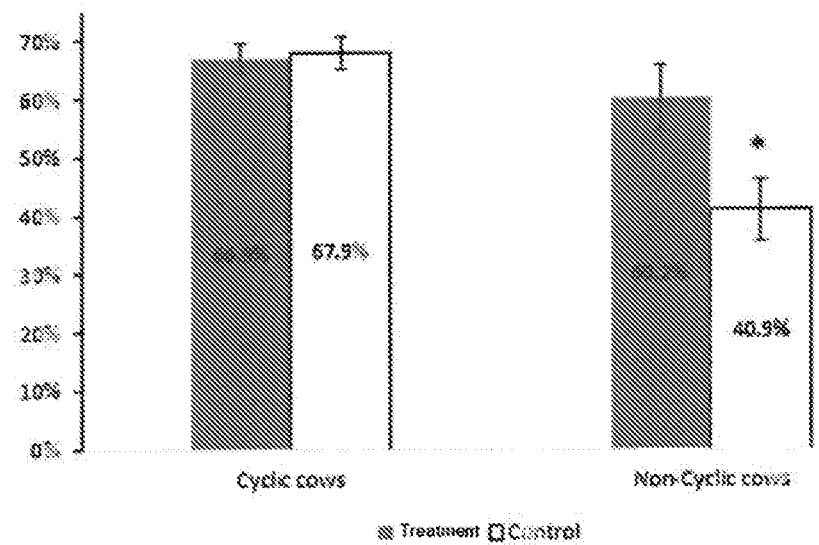
FIG. 4A shows a chart of the probability (estimated marginal means and standard error of the mean (SEM)) of conception to the first insemination and FIG. 4B shows the probability (estimated marginal means and SEM) of pregnancy within 3 weeks after the planned start of the breeding program for cyclic and non-cyclic cows by treatment groups. The asterisk indicates a difference between treatments within the non-cycling group.
Figure 4B:
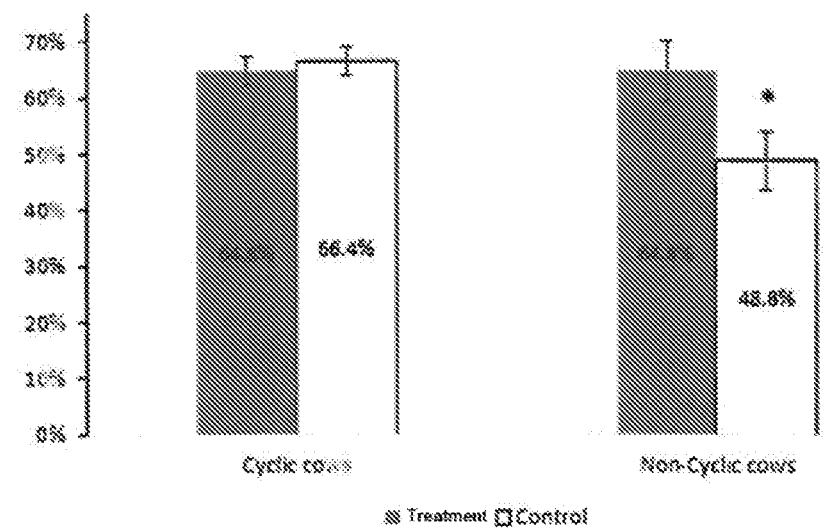

In a multivariable regression analysis that controlled for potential effect modifiers including breed (Holstein, Jersey and crossbred), age (2, 3 and 4+ years), herd (1 and 2), ovarian cyclic activity (cycling and not cycling based on the insertion of a CIDR device) and time from calving to PSM (50 to 71 days and ≥72 days), there was a higher probability of conception to first service and pregnant in 3 weeks for non-cyclic cows in the treated group compared to their counterparts in the control group. FIG. 4A shows a chart of the probability (estimated marginal means and standard error of the mean (SEM)) of conception to the first insemination and FIG. 4B shows the probability (estimated marginal means and SEM) of pregnancy within 3 weeks after the planned start of the breeding program for cyclic and non-cyclic cows by treatment groups. The asterisk indicates a difference between treatments within the non-cycling group. The median time from PSM to pregnancy was 15 and 16 days for the treated and control groups respectively (P=0.27).

Numerically more of the treated cows conceived to first service (69% versus 65%), were pregnant by three (63% versus 61%) and six weeks (80% versus 76%) than the untreated controls. There was a treatment by non-cycling status interaction whereby amongst those cows diagnosed as not detected in oestrus and treated for this condition, the treated cows had a higher first service conception rate and a higher proportion pregnant by three weeks into the breeding program.

What is claimed:

1. A method of increasing the conception rate in one or more cows comprising administering to the cows an effective amount of an immunomodulator composition, wherein the immunomodulator composition comprises: a cationic liposome delivery vehicle, wherein the liposome delivery vehicle comprises one or more pairs of lipids selected from the group consisting of N-[1-(2,3-dioleyloxy)propyl]-N,N,N-trimethylanimonium chloride (DOTMA) and cholesterol; N-[1-(2,3-dioleoyloxy)propyl]N,N,N-trimethylammonium chloride (DOTAP) and cholesterol; 1-[2-(oleoyloxy)ethyl]-2-oleyl-3-(2-hydroxyethyl) imidazolinium chloride (DOTIM) and cholesterol; and dimethyldioctadecylammonium bromide (DDAB) and cholesterol and an isolated bacterially obtained nucleic acid molecule that does not code for an immunogen and has at least 90% sequence identity with the sequence of SEQ ID NO: 1 or SEQ ID NO: 2.

2. The method of claim 1, wherein said nucleic acid molecule comprises at least one immunostimulatory CpG motif and at least one non-immunostimulatory CpG motif.

3. The method of claim 1, wherein the Liposome delivery vehicle comprises one or more lipids selected from the group consisting of multilamellar vesicle lipids and extruded lipids.

4. The method of claim 1, wherein the nucleic acid molecule comprises SEQ ID NO: 1.

5. The method of claim 1, wherein the nucleic acid molecule comprises SEQ ID NO: 2.

6. The method claim 1 wherein the immunomodulator composition further comprises a biological agent.

7. The method of claim 6, wherein the biological agent is selected from the group consisting of immune enhancer proteins, immunogens, vaccines, antimicrobials or any combination thereof.

8. The method of claim 1, wherein the administering is selected from the group consisting of intravenously, intramuscularly, intradermal, intraperitoneal, subcutaneously, by spray-aerosol, orally, intraocularly, intracheally, and intranasal.

9. The method of claim 1 wherein the immunomodulator composition further comprises comprising a pharmaceutically acceptable earner.

10. The method of claim 1 wherein the conception rate in cows increases relative to the conception rate in a control population as measured by a p-value of ≤0.05.

* * * * *